(12) United States Patent
Browning et al.

(10) Patent No.: US 6,869,605 B2
(45) Date of Patent: Mar. 22, 2005

(54) BAFF, INHIBITORS THEREOF AND THEIR USE IN THE MODULATION OF B-CELL RESPONSE

(75) Inventors: Jeffrey Browning, Brookline, MA (US); Christine Ambrose, Reading, MA (US); Fabienne MacKay, Vaucluse (AU); Jurg Tschopp, Epalinges (CH); Pascal Schneider, Epalinges (CH)

(73) Assignee: Biogen Idec Ma Inc., Cambridge, MA (US)

( * ) Notice: Subject to any disclaimer, the term of this patent is extended or adjusted under 35 U.S.C. 154(b) by 0 days.

(21) Appl. No.: 09/911,777

(22) Filed: Jul. 24, 2001

(65) Prior Publication Data

US 2002/0037852 A1 Mar. 28, 2002

Related U.S. Application Data

(60) Provisional application No. 60/117,169, filed on Jan. 25, 1999, and provisional application No. 60/143,228, filed on Jul. 9, 1999.

(51) Int. Cl.[7] .................. A61A 39/395; C07K 16/44
(52) U.S. Cl. ...................... 424/141.1; 424/145.1; 424/177.1; 530/388.23; 530/389.2
(58) Field of Search .................... 424/145.1, 130.1, 424/141.1, 177.1; 530/387.1, 388.1, 388.23, 389.2

(56) References Cited

U.S. PATENT DOCUMENTS

| | | | |
|---|---|---|---|
| 5,595,721 | A | 1/1997 | Kaminski et al. |
| 5,969,102 | A | 10/1999 | Bram et al. |
| 6,297,367 | B1 | 10/2001 | Tribouley |
| 6,316,222 | B1 | 11/2001 | Bram et al. |
| 6,475,986 | B1 | 11/2002 | Aggarwal |
| 6,475,987 | B1 | 11/2002 | Shu |
| 6,541,224 | B2 | 4/2003 | Yu et al. |
| 2003/0023038 | A1 * | 1/2003 | Rennert et al. |

FOREIGN PATENT DOCUMENTS

| | | |
|---|---|---|
| EP | 0 869 180 | 10/1998 |
| EP | 0 921 194 | 6/1999 |
| WO | WO 97/33902 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/11791 | 3/1999 |
| WO | WO 99/12964 | 3/1999 |
| WO | WO 99/12965 | 3/1999 |
| WO | WO 99/33980 | 7/1999 |
| WO | WO 00/26244 | 5/2000 |
| WO | WO 00/39295 | 7/2000 |
| WO | WO 00/40716 | 7/2000 |
| WO | WO 00/43032 | 7/2000 |
| WO | WO 00/50597 | 8/2000 |
| WO | WO 00/50633 | 8/2000 |
| WO | WO 00/68378 | 11/2000 |
| WO | WO 02/02641 | 1/2002 |
| WO | WO 02/18620 | 3/2002 |
| WO | WO 03/055979 | 7/2003 |

OTHER PUBLICATIONS

Furie et al. Safety, Pharmacokinetic and pharmacodynamic results of a phase 1 single and double dose–escalation study of lymphoStat–B in SLE Patients. American College of Rheumatology (ACR), 67th Annual Scientific meeting, Abstract. 922, Oct. 23–28, 2003.*

Wendy et al. Effects of lymphoStat–B, a bLyS Antagonist, when Administered Intravenously to Cynomolgus Monkeys. American College of Rheumatology (ACR), 67th Annual Scientific meeting, Abstract. 1537, Oct. 23–28, 2003.*

Kayagaki et al. BAFF/BLyS receptor 3 binds the B cell survival factor BAFF ligand through a discrete surface loop and promotes processing of NF–kappaB2. Immunity. 17(4):515–524, 2002.*

Colman PM. Effects of amino acid sequence changes on antibody–antigen interactions. Res Immunol. 145(1):33–36, 1994.*

Ward PA, Mulligan MS. Blocking of adhesion molecules in vivo as anti–inflammatory therapy. Ther Immunol 1(3):165–171, 199.*

Harlow E, Lane D.. Antibodies a laboratory manual. Cold Spring Harbor, New York: Cold Spring Harbor Laboratory Press, 198.*

Ware CF. APRIL and BAFF connect autoimmunity and cancer. J Exp Med. 192(11):F35–8, 2000.*

Kogan et al A single amino acid residue can determine the ligand specificity of E–selectin. J Biol Chem. 270(23):14047–55, 199.*

Gras et al., "BCMAp: An Integral Membrane Protein in the Golgi Apparatus of Human Mature B Lymphocytes", International Immunology, vol. 7, No. 7, 1995, pp. 1093–1106.

Gross et al., "TACI and BCMA are Receptors for a TNF Homologue Implicated in B–Cell Autoimmune Disease", Nature, vol. 404, Apr. 27, 2000, pp. 995–999.

Hahne et al., "APRIL, A New Ligand of the Tumor Necrosis Factor Family, Stimulates Tumor Cell Growth", J. Exp. Med., vol. 188, No. 6, Sep. 21, 1998, pp. 1185–1190.

Khare et al., "Severe B Cell Hyperplasia and Autoimmune Disease in TALL–1 Transgenic Mice", Proceedings of the National Academy of Sciences of the United States of America, Mar. 28, 2000, vol. 97, No. 7, pp. 3370–3375.

Kwon et al., "Functions of Newly Identified Members of theTumor Necrosis Factor Receptor/Ligand Superfamilies in Lymphocytes", Current Opinion in Immunology, 1999, pp. 340–345.

(List continued on next page.)

*Primary Examiner*—Christina Chan
*Assistant Examiner*—Maher Haddad
(74) *Attorney, Agent, or Firm*—Finnegan, Henderson, Farabow, Garrett & Dunner, L.L.P.

(57) ABSTRACT

The invention provides methods for treating or preventing disorders associated with expression of BAFF comprising BAFF and fragments thereof, antibodies, agonists and antagonists.

14 Claims, 31 Drawing Sheets

OTHER PUBLICATIONS

Laabi et al., "A New Gene, BCM, on Chromosome 16 is Fused to the Interleukin 2 Gene by a t(4;16) (q26;p13) Translocation in a Malignant T Cell Lymphoma", The EMBO Journal, vol. 11, No. 11, 1992, pp. 3897–3904.

Laabi et al., "The BCMA Gene, Preferentially Expressed During B Lymphoid Maturation, is Bidirectionally Transcribed", Nucleic Acids Research, vol. 22, No. 7, 1994, pp. 1147–1154.

MacKay et al., "Mice Transgenic for BAFF Develop Lymphocytic Disorders along with Autoimmune Manifestations", Journal of Experimental Medicine, Dec. 6, 1999, vol. 190, No. 11, pp. 1697–1710.

Maldry et al., "The Characterization of Murine BCMA Gene Defines it as a New Memer of the Tumor Necrosis Factor Receptor Superfamily", International Immunology, vol. 10, No. 11, 1998, pp. 1693–1702.

Mukhopadhyay et al., "Identification and Characterization of a Novel Cytokine, THANK, a TNF Homologue that Activates Apoptosis, Nuclear Factor–kappaB, and c–Jun NH2–Terminal Kinase", Journal of Biological Chemistry, Jun. 4, 1999, vol. 274, No. 23, pp. 15978–15981.

Moore et al., "BLyS: Member of the Tumor Necrosis Factor Family and B Lymphocyte Stimulator", Science, Jul. 9, 1999, vol. 285, No. 5425, pp. 260–263.

Pitti et al., "Genomic Amplification of a Decoy Receptor for Fas Ligand in Lung and Colon Cancer", Nature, vol. 396, Dec. 17, 1998, pp. 699–703.

Schneider et al., "BAFF, A Novel Ligand of the Tumor Necrosis Factor Family, Stimulates B Cell Growth", J. Exp. Med., vol. 189, No. 11, Jun. 7, 1999, pp. 1747–1756.

Shu et al., "B Cell Maturation Protein is a Receptor for the Tumor Necrosis Factor Family Member TALL–1", PNAS, vol. 97, No. 16, Aug. 1, 2000, pp. 9156–9161.

Thompson et al., "BAFF Interacts with the Orphan Receptor, BCMA", Scandinavian Journal of Immunology, vol. 51 (Supplement 1), 2000, p. 65.

Thompson et al., "BAFF Binds to the Tumor Necrosis Factor Receptor–like Molecule B Cell Maturation Antigen and is Important for Maintaining the Peripheral B Cell Population", J. Exp. Med., vol. 192, No. 1, Jul. 3, 2000, pp. 129–135.

Xia et al., "TACI is a TRAF–Interacting Receptor for TALL–1, a Tumor Necrosis Factor Family Member Involved in B Cell Regulation", J. Exp. Med., vol. 192, No. 1, Jul. 3, 2000, pp. 137–143.

Yu et al., "APRIL and TALL–1 and Receptors BCMA and TACI: System for Regulating Humoral Immunity", Nature Immunology, vol. 1, No. 3, Sep. 2000, pp. 252–256.

Kashii, Y. et al., "Constitutive Expression and Role of the TNF Family Ligands in Apoptotic Killing of Tumor Cells by Human Ink Cells," J. Immunol. 163:5358–66 (1999).

Published U.S. Appl. No. 10/380,703, filed Mar. 17, 2003; Publication No. US–2004–0072188–A1, published Apr. 15, 2004.

Published U.S. Appl. No. 10/077,438, filed Feb. 15, 2002; Publication No. US–2002–0165156–A1, published Nov. 7, 2002.

Published U.S. Appl. No. 10/077,137, filed Feb. 15, 2002; Publication No. US–2002–0172674–A1, published Nov. 21, 2002.

Published U.S. Appl. No. 10/115,192, filed Apr. 2, 2002; Publication No. US–2003–0082175–A1, published May 1, 2003.

Published U.S. Appl. No. 10/214,065, filed Aug. 7, 2002; Publication No. US 2003–0023038–A1, published Jan. 30, 2003.

Published U.S. Appl. No. 10/258,368, filed Jun. 23, 2003; Publication No. US–2004–0013674–A1, published Jan. 22, 2004.

* cited by examiner

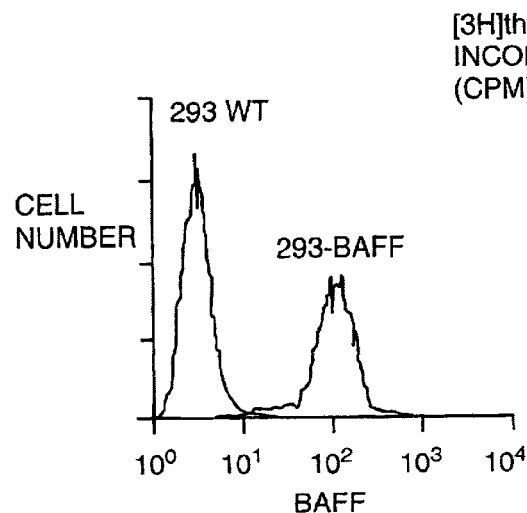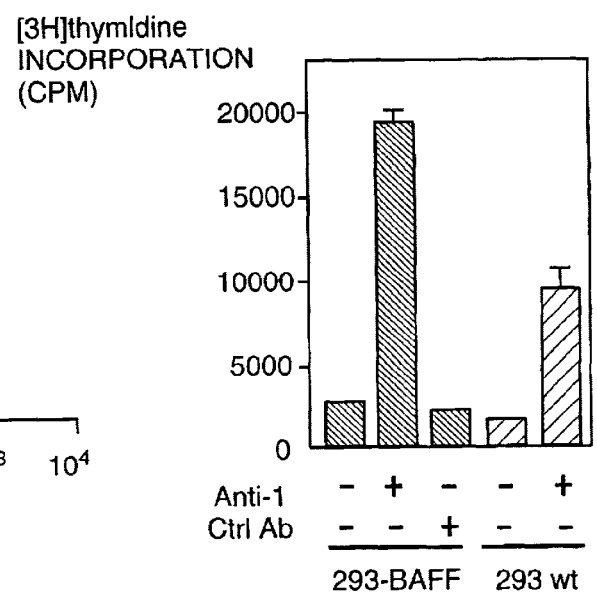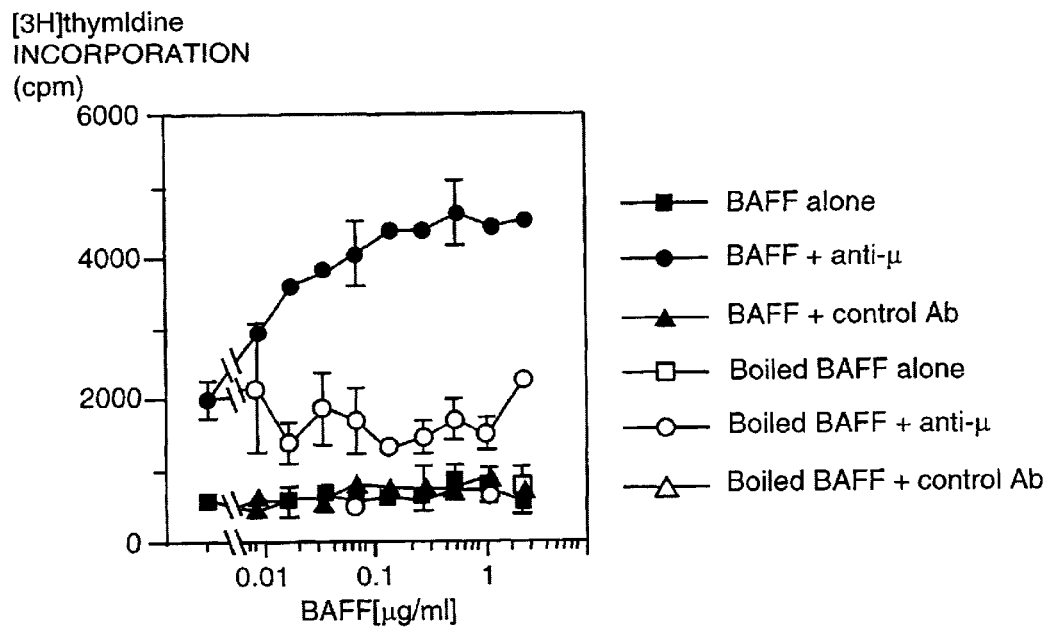
FIG. 5A
FIG. 5B
FIG. 5C

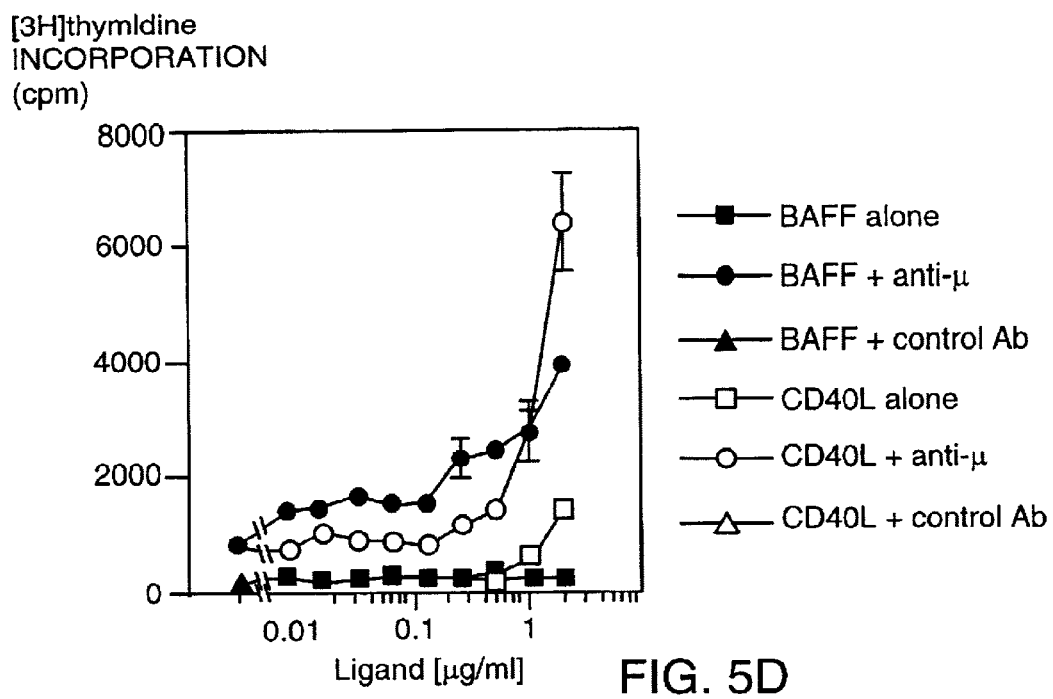
FIG. 5D
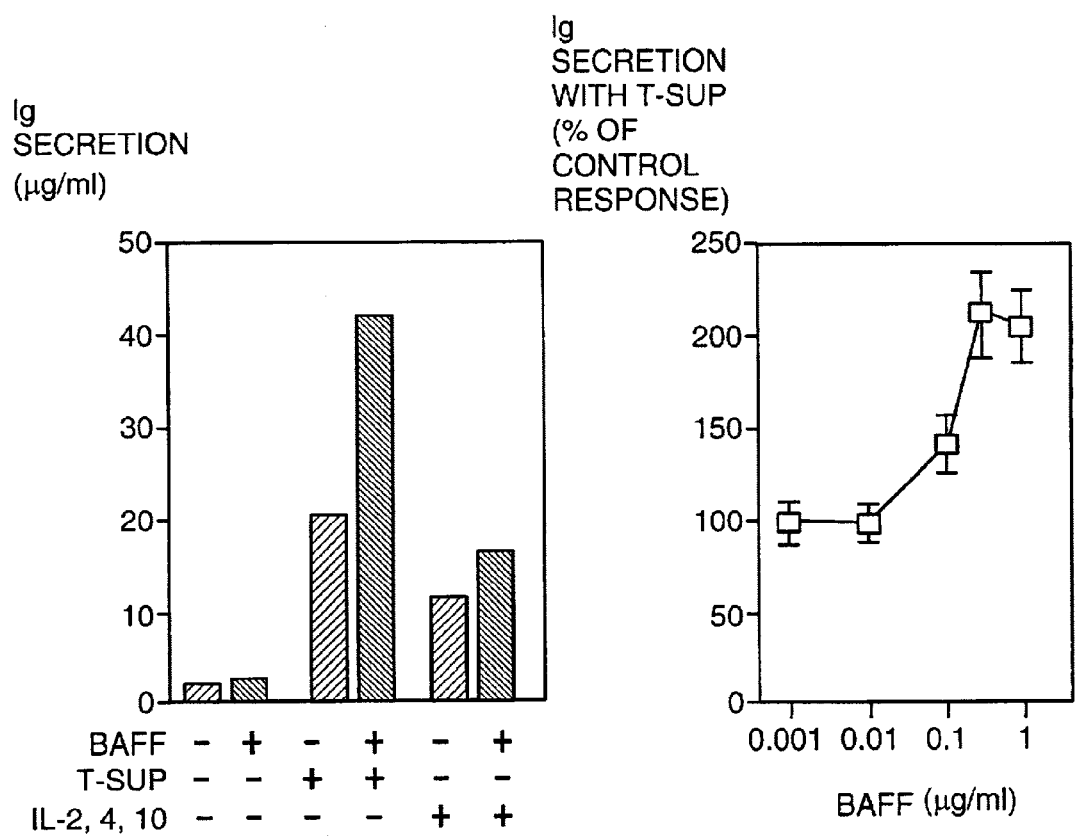
FIG. 5E
FIG. 5F

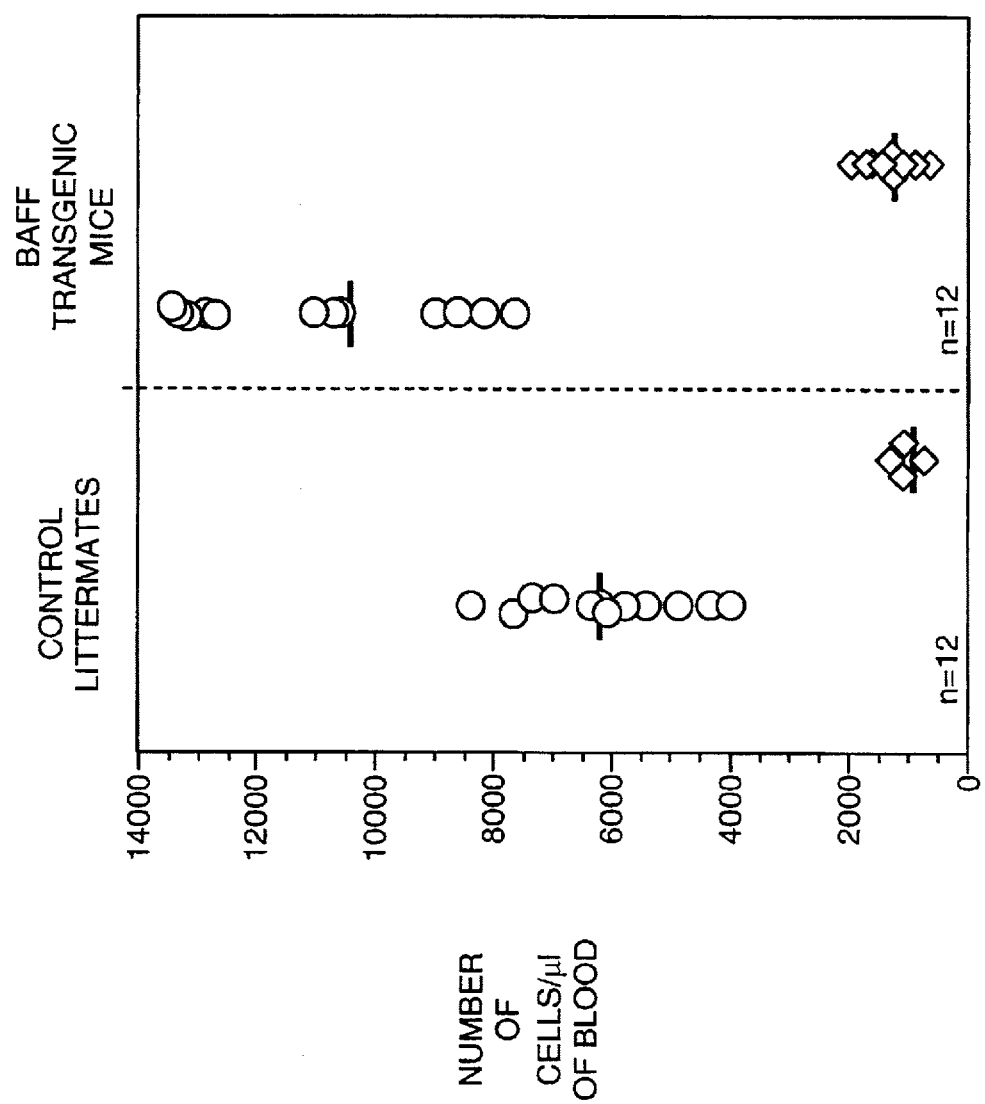

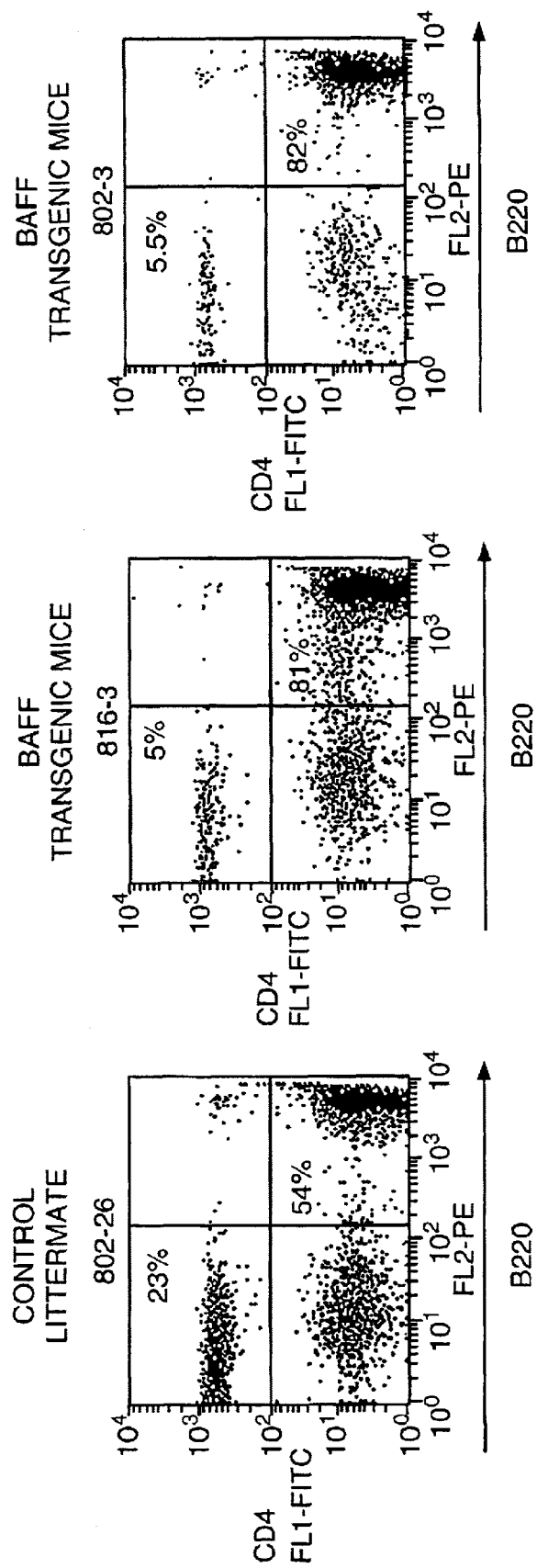

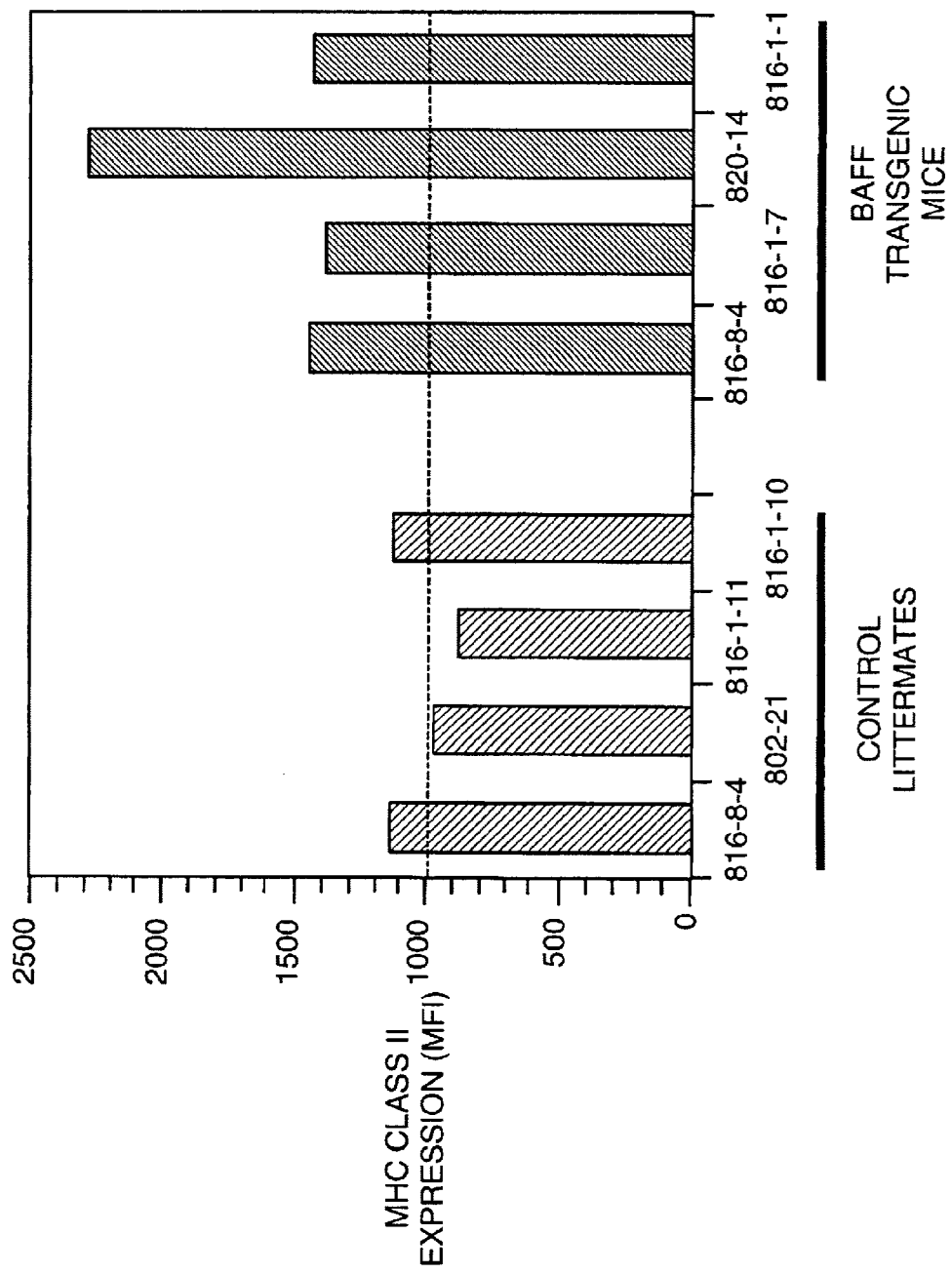

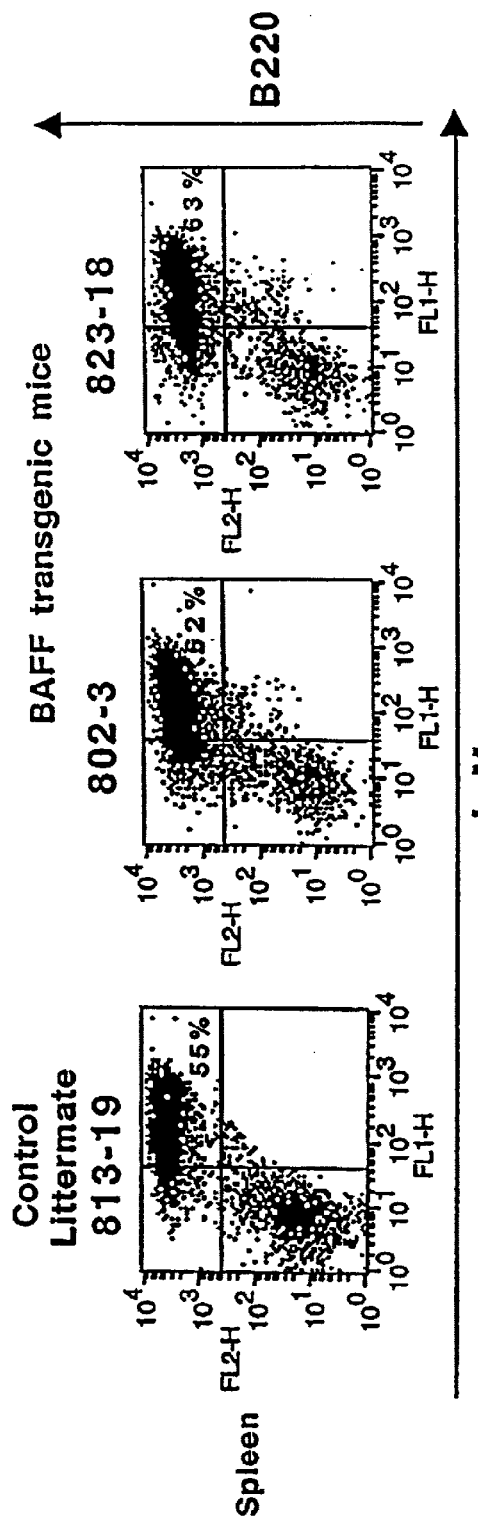
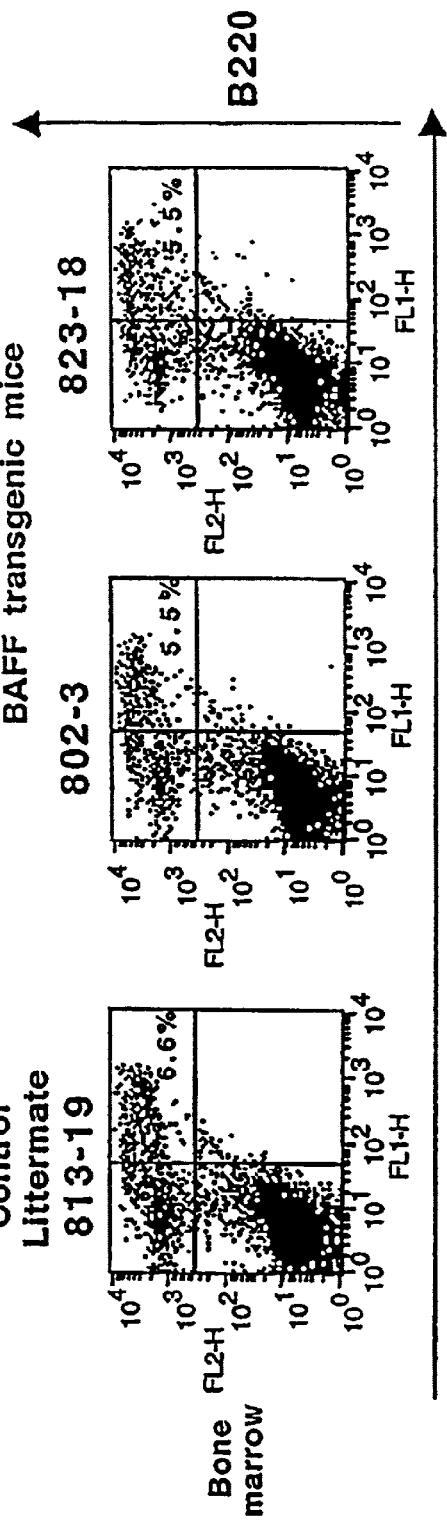
FIG. 8A-1
FIG. 8A-2

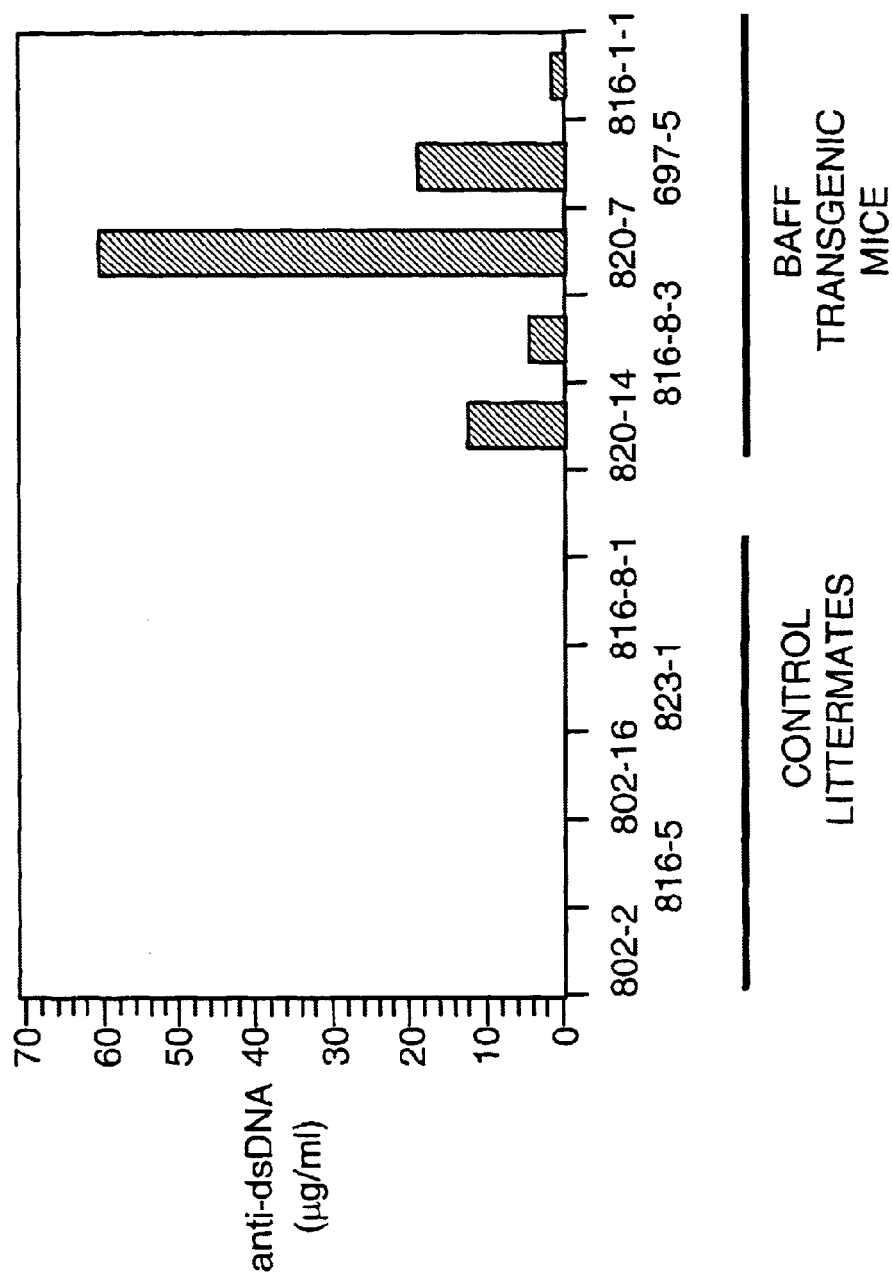

SEQUENCE LISTING

<160> NUMBER OF SEQ ID NOS: 26

<210> SEQ ID NO 1
<211> LENGTH: 285
<212> TYPE: PRT
<213> ORGANISM: Homo sapiens

<400> SEQUENCE: 1

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

```
Phe Phe Ile Tyr Gly Gln Val Leu Tyr Thr Asp Lys Thr Tyr Ala Met
        195                 200                 205
Gly His Leu Ile Gln Arg Lys Lys Val His Val Phe Gly Asp Glu Leu
        210                 215                 220
Ser Leu Val Thr Leu Phe Arg Cys Ile Gln Asn Met Pro Glu Thr Leu
225                 230                 235                 240
Pro Asn Asn Ser Cys Tyr Ser Ala Gly Ile Ala Lys Leu Glu Glu Gly
                245                 250                 255
Asp Glu Leu Gln Leu Ala Ile Pro Arg Glu Asn Ala Gln Ile Ser Leu
        260                 265                 270
Asp Gly Asp Val Thr Phe Phe Gly Ala Leu Lys Leu Leu
        275                 280                 285

<210> SEQ ID NO 2
<211> LENGTH: 309
<212> TYPE: PRT
<213> ORGANISM: Mus sp.

<400> SEQUENCE: 2

Met Asp Glu Ser Ala Lys Thr Leu Pro Pro Cys Leu Cys Phe Cys
1               5                   10                  15
Ser Glu Lys Gly Glu Asp Met Lys Val Gly Tyr Asp Pro Ile Thr Pro
                20                  25                  30
Gln Lys Glu Glu Gly Ala Trp Phe Gly Ile Cys Arg Asp Gly Arg Leu
        35                  40                  45
Leu Ala Ala Thr Leu Leu Ala Leu Leu Ser Ser Phe Thr Ala
        50                  55                  60
Met Ser Leu Tyr Gln Leu Ala Ala Leu Gln Ala Asp Leu Met Asn Leu
65                  70                  75                  80
Arg Met Glu Leu Gln Ser Tyr Arg Gly Ser Ala Thr Pro Ala Ala Ala
                85                  90                  95
Gly Ala Pro Glu Leu Thr Ala Gly Val Lys Leu Leu Thr Pro Ala Ala
                100                 105                 110
Pro Arg Pro His Asn Ser Ser Arg Gly His Arg Asn Arg Arg Ala Phe
        115                 120                 125
Gln Gly Pro Glu Glu Thr Glu Gln Asp Val Asp Leu Ser Ala Pro Pro
        130                 135                 140
Ala Pro Cys Leu Pro Gly Cys Arg His Ser Gln His Asp Asp Asn Gly
145                 150                 155                 160
Met Asn Leu Arg Asn Ile Ile Gln Asp Cys Leu Gln Leu Ile Ala Asp
                165                 170                 175
Ser Asp Thr Pro Thr Ile Arg Lys Gly Thr Tyr Thr Phe Val Pro Trp
        180                 185                 190
Leu Leu Ser Phe Lys Arg Gly Asn Ala Leu Glu Glu Lys Glu Asn Lys
        195                 200                 205
Ile Val Val Arg Gln Thr Gly Tyr Phe Phe Ile Tyr Ser Gln Val Leu
        210                 215                 220
Tyr Thr Asp Pro Ile Phe Ala Met Gly His Val Ile Gln Arg Lys Lys
225                 230                 235                 240
Val His Val Phe Gly Asp Glu Leu Ser Leu Val Thr Leu Phe Arg Cys
                245                 250                 255
Ile Gln Asn Met Pro Lys Thr Leu Pro Asn Asn Ser Cys Tyr Ser Ala
                260                 265                 270
Gly Ile Ala Arg Leu Glu Glu Gly Asp Glu Ile Gln Leu Ala Ile Pro
```

```
                275                 280                 285
Arg Glu Asn Ala Gln Ile Ser Arg Asn Gly Asp Asp Thr Phe Phe Gly
    290                 295                 300

Ala Leu Lys Leu Leu
305

<210> SEQ ID NO 3
<211> LENGTH: 102
<212> TYPE: PRT
<213> ORGANISM: Homo sapiens

<400> SEQUENCE: 3

Val Thr Gln Asp Cys Leu Gln Leu Ile Ala Asp Ser Glu Thr Pro Thr
  1               5                  10                  15

Ile Gln Lys Gly Ser Tyr Thr Phe Val Pro Trp Leu Leu Ser Phe Lys
             20                  25                  30

Arg Gly Ser Ala Leu Glu Glu Lys Tyr Gly Gln Val Leu Tyr Thr Asp
         35                  40                  45

Lys Thr Tyr Ala Met Gly His Leu Ile Gln Arg Lys Lys Val His Val
     50                  55                  60

Phe Gly Asp Glu Leu Ser Asn Asn Ser Cys Tyr Ser Ala Gly Ile Ala
 65                  70                  75                  80

Lys Leu Glu Glu Gly Asp Glu Leu Gln Leu Ala Ile Pro Arg Glu Asn
                 85                  90                  95

Ala Gln Ile Ser Leu Asp
            100

<210> SEQ ID NO 4
<211> LENGTH: 96
<212> TYPE: PRT
<213> ORGANISM: Homo sapiens

<400> SEQUENCE: 4

Lys Gln His Ser Val Leu His Leu Val Pro Ile Asn Ala Thr Ser Lys
  1               5                  10                  15

Asp Asp Ser Asp Val Thr Glu Val Met Trp Gln Pro Ala Leu Arg Arg
             20                  25                  30

Gly Arg Gly Leu Gln Ala Gln Tyr Ser Gln Val Leu Phe Gln Asp Val
         35                  40                  45

Thr Phe Thr Met Gly Gln Val Val Ser Arg Glu Gly Gln Gly Arg Ala
     50                  55                  60

Tyr Asn Ser Cys Tyr Ser Ala Gly Val Phe His Leu His Gln Gly Asp
 65                  70                  75                  80

Ile Leu Ser Val Ile Ile Pro Arg Ala Arg Ala Lys Leu Asn Leu Ser
                 85                  90                  95

<210> SEQ ID NO 5
<211> LENGTH: 104
<212> TYPE: PRT
<213> ORGANISM: Homo sapiens

<400> SEQUENCE: 5

Ser Asp Lys Pro Val Ala His Val Val Ala Asn Pro Gln Ala Glu Gly
  1               5                  10                  15

Gln Leu Gln Trp Leu Asn Arg Arg Ala Asn Ala Leu Leu Ala Asn Gly
             20                  25                  30

Val Tyr Ser Gln Val Leu Phe Lys Gly Gln Gly Cys Pro Ser Thr His
         35                  40                  45
```

-continued

```
Val Leu Leu Thr His Thr Ile Ser Arg Ile Ala Val Ser Tyr Gln Thr
        50                  55                  60
Glu Gly Ala Glu Ala Lys Pro Trp Tyr Glu Pro Ile Tyr Leu Gly Gly
 65                  70                  75                  80
Val Phe Gln Leu Glu Lys Gly Asp Arg Leu Ser Ala Glu Ile Asn Arg
                85                  90                  95
Pro Asp Tyr Leu Asp Phe Ala Glu
            100
```

<210> SEQ ID NO 6
<211> LENGTH: 97
<212> TYPE: PRT
<213> ORGANISM: Homo sapiens

<400> SEQUENCE: 6

```
Glu Leu Arg Lys Val Ala His Leu Thr Gly Lys Ser Asn Ser Arg Ser
 1               5                  10                  15
Met Pro Leu Glu Trp Glu Asp Thr Tyr Gly Ile Val Leu Leu Ser Gly
                20                  25                  30
Val Lys Tyr Ser Lys Val Tyr Phe Arg Gly Gln Ser Cys Asn Asn Leu
            35                  40                  45
Pro Leu Ser His Lys Val Tyr Met Arg Asn Ser Lys Tyr Pro Gln Met
        50                  55                  60
Trp Ala Arg Ser Ser Tyr Leu Gly Ala Val Phe Asn Leu Thr Ser Ala
 65                  70                  75                  80
Asp His Leu Tyr Val Asn Val Ser Glu Leu Ser Leu Val Asn Phe Glu
                85                  90                  95
Glu
```

<210> SEQ ID NO 7
<211> LENGTH: 102
<212> TYPE: PRT
<213> ORGANISM: Homo sapiens

<400> SEQUENCE: 7

```
Thr Leu Lys Pro Ala Ala His Leu Ile Gly Asp Pro Ser Lys Gln Asn
 1               5                  10                  15
Ser Leu Leu Trp Arg Ala Asn Thr Asp Arg Ala Phe Leu Gln Asp Gly
                20                  25                  30
Phe Tyr Ser Gln Val Val Phe Ser Gly Lys Ala Tyr Ser Pro Lys Ala
            35                  40                  45
Thr Ser Ser Pro Leu Tyr Leu Ala His Glu Val Gln Leu Phe Ser Ser
        50                  55                  60
Gln Tyr Pro Phe Pro Trp Leu His Ser Met Tyr His Gly Ala Ala Phe
 65                  70                  75                  80
Gln Leu Thr Gln Gly Asp Gln Leu Ser Thr His Thr Asp Gly Ile Pro
                85                  90                  95
His Leu Val Leu Ser Phe
            100
```

<210> SEQ ID NO 8
<211> LENGTH: 109
<212> TYPE: PRT
<213> ORGANISM: Homo sapiens

<400> SEQUENCE: 8

```
Glu Ala Gln Pro Phe Ala His Leu Thr Ile Asn Ala Thr Asp Ile Pro
```

```
                1               5                  10                 15
Ser Gly Ser His Lys Val Ser Leu Ser Ser Trp Tyr His Asp Arg Gly
                        20                  25                  30

Trp Gly Lys Ile Ser Asn Met Tyr Ala Asn Ile Cys Phe Arg His His
            35                  40                  45

Glu Thr Ser Gly Asp Leu Ala Thr Glu Tyr Leu Gln Leu Met Val Tyr
    50                  55                  60

Val Thr Lys Thr Ser Ile Lys Ile Pro Ser Glu Phe His Phe Tyr Ser
65                  70                  75                  80

Ile Asn Val Gly Gly Phe Phe Lys Leu Arg Ser Gly Glu Glu Ile Ser
                85                  90                  95

Ile Glu Val Ser Asn Pro Ser Leu Leu Asp Pro Asp Gln
            100                 105
```

<210> SEQ ID NO 9
<211> LENGTH: 26
<212> TYPE: DNA
<213> ORGANISM: Homo sapiens

<400> SEQUENCE: 9
actgtttctt ctggaccctg aacggc                                  26

<210> SEQ ID NO 10
<211> LENGTH: 30
<212> TYPE: DNA
<213> ORGANISM: Homo sapiens

<400> SEQUENCE: 10
gacaagcttg ccaccatgga tgactccaca                              30

<210> SEQ ID NO 11
<211> LENGTH: 23
<212> TYPE: DNA
<213> ORGANISM: Homo sapiens

<400> SEQUENCE: 11
actagtcaca gcagtttcaa tgc                                     23

<210> SEQ ID NO 12
<211> LENGTH: 22
<212> TYPE: DNA
<213> ORGANISM: Homo sapiens

<400> SEQUENCE: 12
ctgcagggtc cagaagaaac ag                                      22

<210> SEQ ID NO 13
<211> LENGTH: 24
<212> TYPE: DNA
<213> ORGANISM: Homo sapiens

<400> SEQUENCE: 13
ggagaaggca actccagtca gaac                                    24

<210> SEQ ID NO 14
<211> LENGTH: 24
<212> TYPE: DNA
<213> ORGANISM: Homo sapiens

<400> SEQUENCE: 14
caattcatcc ccaaagacat ggac                                    24

-continued

<210> SEQ ID NO 15
<211> LENGTH: 22
<212> TYPE: DNA
<213> ORGANISM: Homo sapiens

<400> SEQUENCE: 15
tcggaacaca acgaaacaag tc                                        22

<210> SEQ ID NO 16
<211> LENGTH: 26
<212> TYPE: DNA
<213> ORGANISM: Homo sapiens

<400> SEQUENCE: 16
cttctccttc acctggaaac tgactg                                    26

<210> SEQ ID NO 17
<211> LENGTH: 19
<212> TYPE: DNA
<213> ORGANISM: Homo sapiens

<400> SEQUENCE: 17
ggcatcgtga tggactccg                                            19

<210> SEQ ID NO 18
<211> LENGTH: 19
<212> TYPE: DNA
<213> ORGANISM: Homo sapiens

<400> SEQUENCE: 18
gctggaaggt ggacagcga                                            19

<210> SEQ ID NO 19
<211> LENGTH: 35
<212> TYPE: DNA
<213> ORGANISM: Homo sapiens

<400> SEQUENCE: 19
taagaatgcg gccgcggaat ggatgagtct gcaaa                          35

<210> SEQ ID NO 20
<211> LENGTH: 35
<212> TYPE: DNA
<213> ORGANISM: Homo sapiens

<400> SEQUENCE: 20
taagaatgcg gccgcgggat cacgcactcc agcaa                          35

<210> SEQ ID NO 21
<211> LENGTH: 21
<212> TYPE: DNA
<213> ORGANISM: Homo sapiens

<400> SEQUENCE: 21
gcagtttcac agcgatgtcc t                                         21

<210> SEQ ID NO 22
<211> LENGTH: 21
<212> TYPE: DNA
<213> ORGANISM: Homo sapiens

<400> SEQUENCE: 22

-continued

```
gtctccgttg cgtgaaatct g                                    21

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 23

Arg Asn Lys Arg
 1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 24

Arg Lys Arg Arg
 1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 25

Arg Pro Arg Arg
 1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      Illustrative motif
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (3)
<223> OTHER INFORMATION: Lys or Arg

<400> SEQUENCE: 26

Arg Xaa Xaa Arg
 1
```

BAFF, INHIBITORS THEREOF AND THEIR USE IN THE MODULATION OF B-CELL RESPONSE

RELATED APPLICATIONS

This application is a continuation of and claims priority to International Application No. PCT/US00/01788 filed Jan. 25, 2000, which claims priority to U.S. Ser. No. 60/117,169 filed on Jan. 25, 1999 and U.S. Ser. No. 60/143,228 filed Jul. 9, 1999. The entire disclosures of the aforesaid patent applications are incorporated herein by reference.

FIELD OF THE INVENTION

The present invention relates to the use of a ligand, BAFF, a β-cell activating factor belonging to the Tumor Necrosis Family and its blocking agents to either stimulate or inhibit the expression of B-cells and immunoglobulins. This protein and its receptor may have anti-cancer and/or immunoregulatory applications as well as uses for the treatment of immunosuppressive disorders such as HIV. Specifically, the ligand and its blocking agents may play a role in the development of hypertension and its related disorders. Furthermore, cells transfected with the gene for this ligand may be used in gene therapy to treat tumors, autoimmune diseases or inherited genetic disorders involving B-cells. Blocking agents, such as recombinant variants or antibodies specific to the ligand or its receptor, may have immunoregulatory applications as well. Use of BAFF as a B-cell stimulator for immune suppressed diseases including for example uses for patients undergoing organ transplantation (ie bone marrow transplant) as well as recovering from cancer treatments to stimulate production of B-cells are contemplated. Use of BAFF as an adjuvant and or costimulator to boast and or restore B cells levels to approximate normal levels are also contemplated.

BACKGROUND OF THE INVENTION

The tumor-necrosis factor (TNF)-related cytokines are mediators of host defense and immune regulation. Members of this family exist in membrane-anchored forms, acting locally through cell-to-cell contact, or as secreted proteins capable of diffusing to more distant targets. A parallel family of receptors signals the presence of these molecules leading to the initiation of cell death or cellular proliferation and differentiation in the target tissue. Presently, the TNF family of ligands and receptors has at least 11 recognized receptor-ligand pairs, including: TNF:TNF-R; LT-α:TNF-R; LT-α/β:LT-β-R; FasL:Fas; CD40L:CD40; CD30L:CD30; CD27L:CD27; OX40L:OX40 and 4-1BBL:4–1BB. The DNA sequences encoding these ligands have only about 25% to about 30% identity in even the most related cases, although the amino acid relatedness is about 50%.

The defining feature of this family of cytokine receptors is found in the cysteine rich extracellular domain initially revealed by the molecular cloning of two distinct TNF receptors. This family of genes encodes glycoproteins characteristic of Type I transmembrane proteins with an extracellular ligand binding domain, a single membrane spanning region and a cytoplasmic region involved in activating cellular functions. The cysteine-rich ligand binding region exhibits a tightly knit disulfide linked core domain, which, depending upon the particular family member, is repeated multiple times. Most receptors have four domains, although there may be as few as three, or as many as six.

Proteins in the TNF family of ligands are characterized by a short N-terminal stretch of normally short hydrophilic amino acids, often containing several lysine or arginine residues thought to serve as stop transfer sequences. Next follows a transmembrane region and an extracellular region of variable length, that separates the C-terminal receptor binding domain from the membrane. This region is sometimes referred to as the "stalk". The C-terminal binding region comprises the bulk of the protein, and often, but not always, contains glycosylation sites. These genes lack the classic signal sequences characteristic of type I membrane proteins, type II membrane proteins with the C terminus lying outside the cell, and a short N-terminal domain residing in the cytoplasm. In some cases, e.g., TNF and LT-α, cleavage in the stalk region can occur early during protein processing and the ligand is then found primarily in secreted form. Most ligands, however, exist in a membrane form, mediating localized signaling.

The structure of these ligands has been well-defined by crystallographic analyses of TNF, LT-α, and CD40L. TNF and lymphotoxin-I (LT-I) are both structured into a sandwich of two anti-parallel β-pleated sheets with the "jelly roll" or Greek key topology. The rms deviation between the Cα and β residues is 0.61 C, suggesting a high degree of similarity in their molecular topography. A structural feature emerging from molecular studies of CD40L, TNF and LT-α is the propensity to assemble into oligomeric complexes. Intrinsic to the oligomeric structure is the formation of the receptor binding site at the junction between the neighboring subunits creating a multivalent ligand. The quaternary structures of TNF, CD40L and LTα have been shown to exist as trimers by analysis of their crystal structures. Many of the amino acids conserved between the different ligands are in stretches of the scaffold β-sheet. It is likely that the basic sandwich structure is preserved in all of these molecules, since portions of these scaffold sequences are conserved across the various family members. The quaternary structure may also be maintained since the subunit conformation is likely to remain similar.

TNF family members can best be described as master switches in the immune system controlling both cell survival and differentiation. Only TNF and LTα, are currently recognized as secreted cytokines contrasting with the other predominantly membrane anchored members of the TNF family. While a membrane form of TNF has been well-characterized and is likely to have unique biological roles, secreted TNF functions as a general alarm signaling to cells more distant from the site of the triggering event. Thus TNF secretion can amplify an event leading to the well-described changes in the vasculature lining and the inflammatory state of cells. In contrast, the membrane bound members of the family send signals though the TNF type receptors only to cells in direct contact. For example T cells provide CD40 mediated "help" only to those B cells brought into direct contact via cognate TCR interactions. Similar cell-cell contact limitations on the ability to induce cell death apply to the well-studied Fas system.

It appears that one can segregate the TNF ligands into three groups based on their ability to induce cell death. First, TNF, Fas ligand and TRAIL can efficiently induce cell death in many lines and their receptors mostly likely have good canonical death domains. Presumably the ligand to DR-3 (TRAMP/WSL-1) would also all into this category. Next there are those ligands which trigger a weaker death signal limited to few cell types and TWEAK, CD30 ligand and LTa1b2 are examples of this class. How this group can trigger cell death in the absence of a canonical death domain is an interesting question and suggests that a separate weaker death signaling mechanism exists. Lastly, there are those members that cannot efficiently deliver a death signal. Probably all groups can have antiproliferative effects on some cell types consequent to inducing cell differentiation e.g. CD40. Funakoshi et al. (1994).

The TNF family has grown dramatically in recent years to encompass at least 11 different signaling pathways involving regulation of the immune system. The widespread expression patterns of TWEAK and TRAIL indicate that there is still more functional variety to be uncovered in this family. This aspect has been especially highlighted recently in the discovery of two receptors that affect the ability of rous sacroma and herpes simplex virus to replicate as well as the historical observations that TNF has anti-viral activity and pox viruses encode for decoy TNF receptors. Brojatsch et al. (1996); Montgomery et al. (1996); Smith et al. (1994), 76 Cell 959–962; Vassalli et al. (1992), 10 Immunol. 411–452.

TNF is a mediator of septic shock and cachexia, and is involved in the regulation of hematopoietic cell development. It appears to play a major role as a mediator of inflammation and defense against bacterial, viral and parasitic infections as well as having antitumor activity. TNF is also involved in different autoimmune diseases. TNF may be produced by several types of cells, including macrophages, fibroblasts, T cells and natural killer cells. TNF binds to two different receptors, each acting through specific intracellular signaling molecules, thus resulting in different effects of TNF. TNF can exist either as a membrane bound form or as a soluble secreted cytokine.

LT-I shares many activities with TNF, i.e. binding to the TNF receptors, but unlike TNF, appears to be secreted primarily by activated T cells and some β-lymphoblastoid tumors. The heteromeric complex of LT-α, and LT-β is a membrane bound complex which binds to the LT-βreceptor. The LT system (LTs and LT-R) appears to be involved in the development of peripheral lymphoid organs since genetic disruption of LT-β leads to disorganization of T and B cells in the spleen and an absence of lymph nodes. The LT-β system is also involved in cell death of some adenocarcinoma cell lines.

Fas-L, another member of the TNF family, is expressed predominantly on activated T cells. It induces the death of cells bearing its receptor, including tumor cells and HIV-infected cells, by a mechanism known as programmed cell death or apoptosis. Furthermore, deficiencies in either Fas or Fas-L may lead to lymphoproliferative disorders, confirming the role of the Fas system in the regulation of immune responses. The Fas system is also involved in liver damage resulting from hepatitis chronic infection and in autoimmunity in HIV-infected patients. The Fas system is also involved in T-cell destruction in HIV patients. TRAIL, another member of this family, also seems to be involved in the death of a wide variety of transformed cell lines of diverse origin.

CD40-L, another member of the TNF family, is expressed on T cells and induces the regulation of CD40-bearing B cells. Furthermore, alterations in the CD40-L gene result in a disease known as X-linked hyper-IgM syndrome. The CD40 system is also involved in different autoimmune diseases and CD40-L is known to have antiviral properties. Although the CD40 system is involved in the rescue of apoptotic B cells, in non-immune cells it induces apoptosis. Many additional lymphocyte members of the TNF family are also involved in costimulation.

Generally, the members of the TNF family have fundamental regulatory roles in controlling the immune system and activating acute host defense systems. Given the current progress in manipulating members of the TNF family for therapeutic benefit, it is likely that members of this family may provide unique means to control disease. Some of the ligands of this family can directly induce the apoptotic death of many transformed cells e.g. LT, TNF, Fas ligand and TRAIL. Nagata (1997) 88 Cell 355–365. Fas and possibly TNF and CD30 receptor activation can induce cell death in nontransformed lymphocytes which may play an immunoregulatory function. Amakawa et al. (1996) 84 Cell 551–562; Nagata (1997) 88 Cell 355–365; Sytwu et al. (1996); Zheng et al. (1995) 377 Nature 348–351. In general, death is triggered following the aggregation of death domains which reside on the cytoplasmic side of the TNF receptors. The death domain orchestrates the assembly of various signal transduction components which result in the activation of the caspase cascade. Nagata (1997) 88 Cell 355–365. Some receptors lack canonical death domains, e.g. LTb receptor and CD30 (Browning et al. (1996); Lee et al. (1996)) yet can induce cell death, albeit more weakly. It is likely that these receptors function primarily to induce cell differentiation and the death is an aberrant consequence in some transformed cell lines, although this picture is unclear as studies on the CD30 null mouse suggest a death role in negative selection in the thymus. Amakawa et al. (1996) 84 Cell 551–562. Conversely, signaling through other pathways such as CD40 is required to maintain cell survival. Thus, there is a need to identify and characterize additional molecules which are members of the TNF family thereby providing additional means of controlling disease and manipulating the immune system.

Here we characterize the functional properties of a new ligand of the TNF cytokine family. The new ligand, termed BAFF (B cell activating factor belonging to the TNF family), appears to be expressed by T cells and dendritic cells for the purpose of B-cell co-stimulation and may therefore play an important role in the control of B cell function. In addition, we have generated transgenic mice overexpressing BAFF under the control of a liver-specific promoter. These mice have excessive numbers of mature B cells, spontaneous germinal center reactions, secrete autoantibodies, and have high plasma cell numbers in secondary lymphoid organs and Ig deposition in the kidney.

SUMMARY OF THE INVENTION

Accordingly, the present invention is directed to the use of BAFF-ligands, blocking agents and antibodies for the ligand, to either stimulate or inhibit the growth of B-cells and the secretion of immunoglobulin. The claimed invention may be used for therapeutic applications in numerous diseases and disorders, as discussed in more detail below, as well as to obtain information about, and manipulate, the immune system and its processes. Further, this invention can be used as a method of stimulating or inhibiting the growth of B-cells and the secretion of immunoglobulins. BAFF associated molecules, as described by this invention, may also have utility in the treatment of autoimmune diseases, disorders relating to B-cell proliferation and maturation, BAFF ligand regulation and inflammation. The invention may be involved in the regulation or prevention of hypertension and hypertension-related disorders of the renal and cardiovascular tissue.

Additional features and advantages of the invention will be set forth in the description which follows, and in part will be apparent from the description, or may be learned by practice of the invention. The objectives and other advantages of the invention will be realized and attained by the methods particularly pointed out in the written description and claims hereof, as well as in the appended drawings.

Thus, to achieve these and other advantages, and in accordance with the purpose of the invention, as embodied and broadly described herein, the invention includes a method of effecting B-cell growth and secretion of immunoglobulins through the administration of various BAFF ligands and related molecules.

The invention also contemplates stimulating B-cell growth through the use of BAFF ligands or active fragments of the polypeptide. The polypeptide may be use alone or with a CD40 ligand or an anti-murine antibody.

In other embodiments, the invention relates to methods of stimulation of dendritic cell-induced B-cell growth and maturation through the use of BAFF ligands or active fragments of BAFF. Again, the polypeptide may be used alone or with CD40 ligand or anti-μ antibodies.

In other embodiments, blocking agents of BAFF and the BAFF receptor have been used to inhibit B-cell growth and immunoglobulin secretion. These agents can be inoperable, recombinant BAFF, BAFF specific antibodies, BAFF-receptor specific antibodies or an anti-BAFF ligand molecule.

In yet other embodiments, the invention relates to the use of BAFF, BAFF related molecules and BAFF blocking agents to treat hypertension, hypertension related disorders, immune disorders, autoimmune diseases, inflammation and B-cell lympho-proliferate disorders.

The invention encompasses the use of BAFF and BAFF-related molecules as either agonists or antagonists in effecting immune responses by effecting the growth and/or maturation of B-cells and secretion of immunoglobulin.

The invention relates in other embodiments to soluble constructs comprising BAFF which may be used to directly trigger BAFF mediated pharmacological events. Such events may have useful therapeutic benefits in the treatment of cancer, tumors or the manipulation of the immune system to treat immunologic diseases.

Additionally, in other embodiments the claimed invention relates to antibodies directed against BAFF ligand, which can be used, for example, for the treatment of cancers, and manipulation of the immune system to treat immunologic disease.

In yet other embodiments the invention relates to methods of gene therapy using the genes for BAFF.

The pharmaceutical preparations of the invention may, optionally, include pharmaceutically acceptable carriers, adjuvants, fillers, or other pharmaceutical compositions, and may be administered in any of the numerous forms or routes known in the art.

It is to be understood that both the foregoing general description and the following detailed description are exemplary and explanatory, and are intended to provide further explanation of the invention as claimed.

The accompanying drawings are included to provide a further understanding of the invention, and are incorporated in, and constitute a part of this specification, illustrate several embodiments of the invention, and together with the description serve to explain the principles of the invention.

DESCRIPTION OF THE DRAWINGS

FIG. 5 depicts BAFF costimulates B cell proliferation. (A) Surface expression of BAFF in stably transfected 293 cells. 293-BAFF and 293 wild-type cells were stained with anti-BAFF mAb 43.9 and analyzed by flow cytometry. (B) Costimulation of PBLs by 293-BAFF cells. PBLs ($10^5$/well) were incubated with 15.000 glutaraldehyde-fixed 293 cells (293 wt or 293-BAFF) in the presence or absence of anti-B cell receptor antibody (anti-p). Fixed 293 cells alone incorporated 100 cpm. (C) Dose dependent costimulation of PBL proliferation by soluble BAFF in the presence of anti-μ.

Figure 1C:
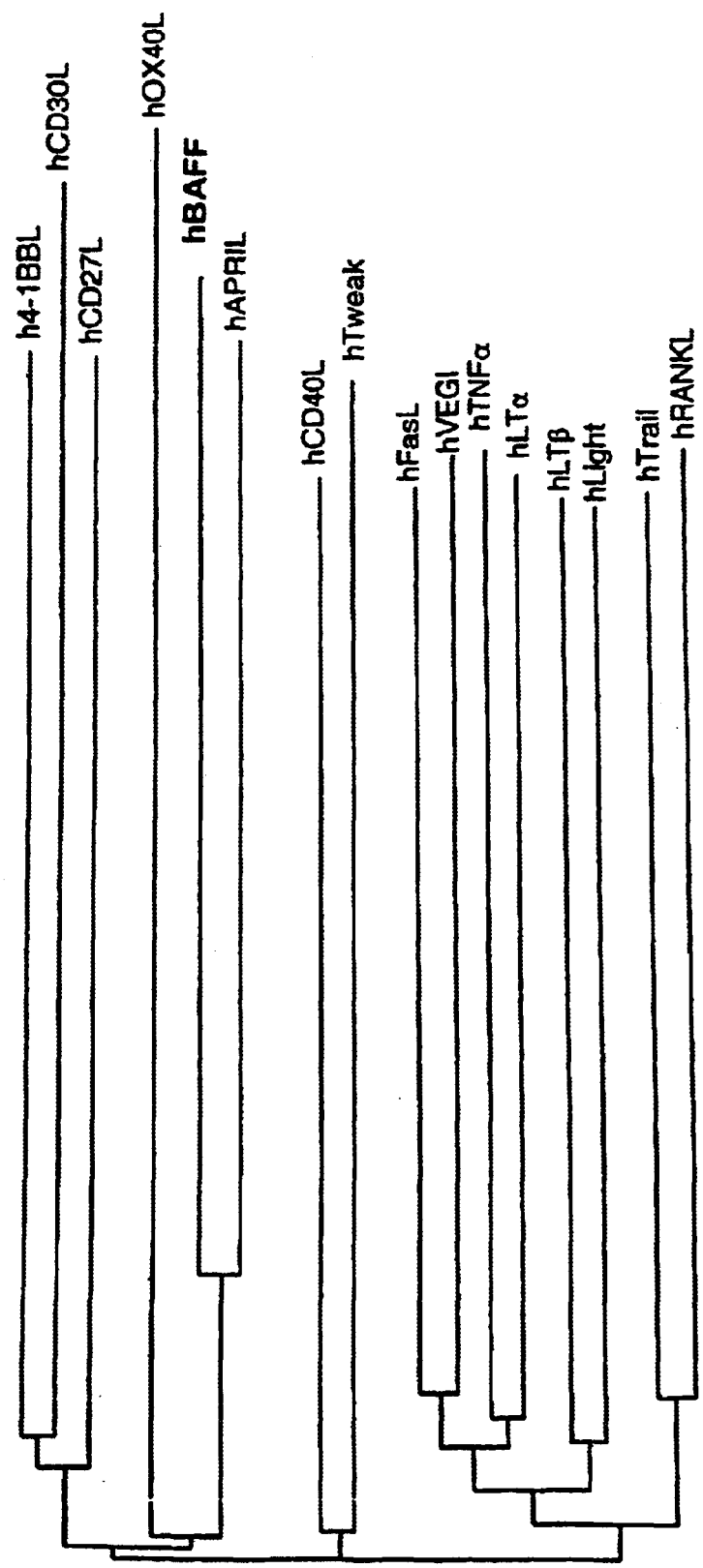
FIG. 1 (A) depicts the predicted amino acid sequence of human [SEQ. ID. NO.: 1] and mouse BAFF [SEQ. ID. NO.:2]. The predicted transmembrane domain (TMD, dashed line), the potential N-linked glycosylation sites (stars) and the natural processing site of human BAFF (arrow) are indicated. The double line above hBAFF indicates the sequence obtained by Edman degradation of the processed form of BAFF. (B) Depicts a comparison of the extracellular protein sequence of BAFF [SEQ. ID. NO.: 3] and some members of the TNF ligand family [SEQ. ID. NO.: 4 (hAPRIL); SEQ. ID. NO.: 5 (hTNF alpha); SEQ. ID. NO.: 6 (hFasL); SEQ. ID. NO.: 7 (hLT alpha); SEQ. ID. NO.: 8 (hRANKL)]. Identical and homologous residues are represented in black and shaded boxes, respectively. (C) Depicts dendrogram of TNF family ligands

Proliferation was determined after 72 h incubation by [$^3$H]-thymidine incorporation. Controls include cells treated with BAFF alone, with heat-denatured BAFF or with an irrelevant isotype matched antibody in place of anti-$\mu$. (D) Comparison of (co)stimulatory effects of sCD40L and sBAFF on PBL proliferation. Experiment was performed as described in panel C. (E) BAFF costimulates Ig secretion of preactivated human B cells. Purified CD19$^+$ B cells were activated by coculture with EL-4 T cells and activated T cell supernatants for 5-6 d, then re-isolated and cultured for another 7 days in the presence of medium only (−) or containing 5% activated T cell supernatants (T-SUP) or a blend of cytokines (IL-2, IL-4, IL-10). The columns represent means of Ig concentrations for cultures with or without 1 $\mu$g/ml BAFF. Means± SD in terms of "fold increase" were 1.23±0.11 for medium only, 2.06±0.18 with T cell supernatants (4 experiments) and 1.45±0.06 with IL-2, IL-4 and IL-10 (2 experiments). These were performed with peripheral blood (3 experiments) or cord blood B cells (one experiment; 2.3 fold increase with T cell supernatants, 1.5 fold increase with IL-2, IL-4 and IL-10). (F) Dose-response curve for the effect of BAFF in cultures with T cell supernatants, as shown in panel D. Mean± SD of 3 experiments.

Figure 6:
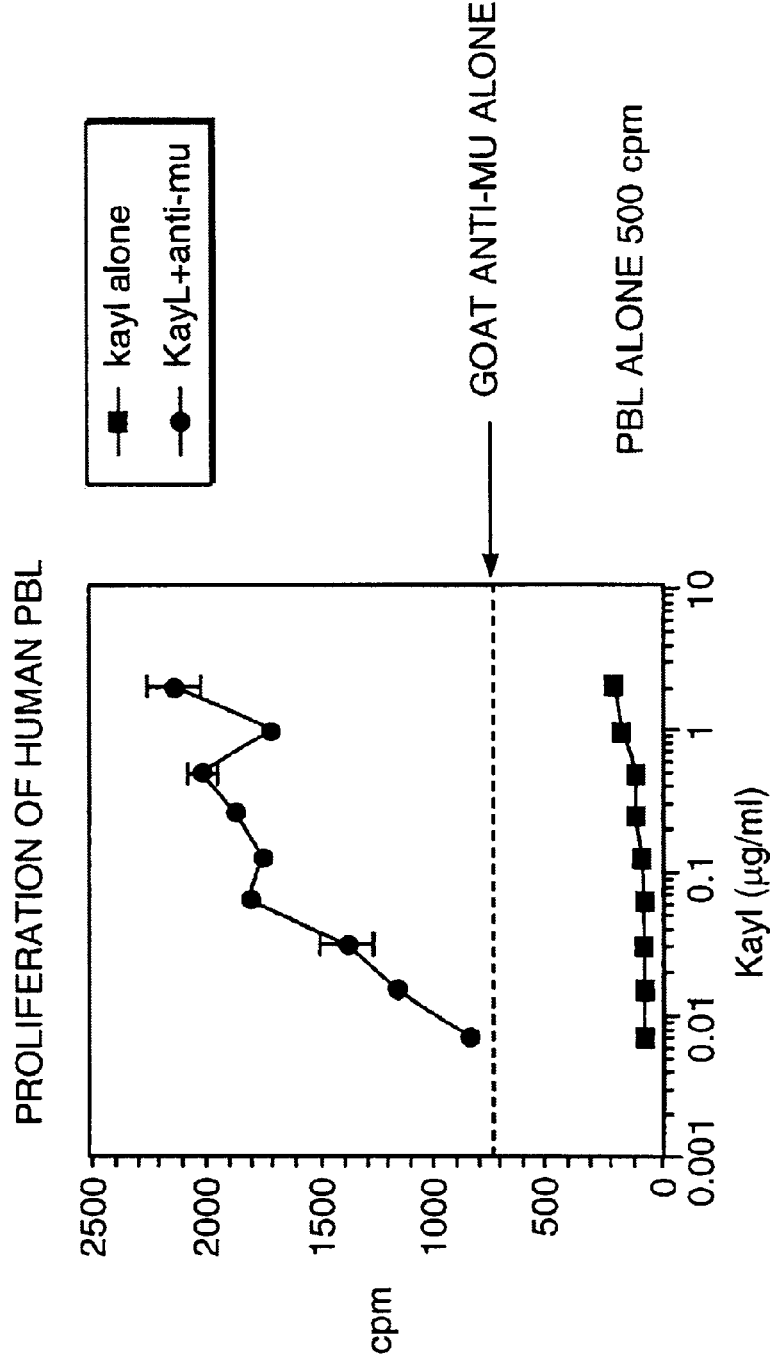

FIG. 6 depicts that BAFF acts as a cofactor for B cell proliferation. The proliferation of human PBL was measured alone (500 cpm), with the presence of BAFF ligand alone, with the presence of goat anti-murine (mu) alone, and with both BAFF ligand and anti-mu. The combination of both anti-mu and BAFF significantly raised proliferation of PBL as the concentration of BAFF increased suggesting BAFF's cofactor characteristics.

FIG. 7 depicts increased B cell numbers in BAFF Tg mice.
(A) Increased lymphocytes counts in BAFF Tg mice. The graph compares 12 control littermates (left panel) with 12 BAFF Tg mice (right panel). Lymphocytes counts are shown with circles and granulocytes (including neutrophils, eosinophils, basophils) with diamonds.
(B) Increased proportion of B cells in PBL from BAFF Tg mice. PBL were stained with both anti-B220-FITC and anti-CD4-PE for FACS analysis and gated on live cells using the forward side scatter. Percentages of CD4 and B220 positive cells are indicated. One control mouse (left) and two BAFF Tg mice (right) are shown and the results were representative of 7 animals analysed in each group.
(C) FACS analysis of the ratio of B to T cells in PBL. The difference between control animals and BAFF Tg mice in (A) and (C) was statistically significant (P<0.001).
(D) Increased MHC class II expression on B cells from BAFF Tg mice PBL.
MHC class II expression was analysed by FACS.
(E) Increased Bcl-2 expression in B cells from BAFF Tg mice PBL.
Bcl-2 expression was measured by intracytoplasmic staining and cells were analysed by FACS. In both (D) and (E) Live cells were gated on the forward side scatter. Four control littermates (white bars) and 4 BAFF Tg mice are shown and are representative of at least 12 animals analysed for each group. MFI: mean of fluorescence intensity. The difference between control animals and BAFF Tg mice was statistically significant (P<0.005).
(F) Increased expression of effector T cells in BAFF Tg mice. PBL were stained with anti-CD4-Cychrome, anti-CD44-FITC and anti-L selectin-PE. Are shown CD4$^+$-gated cells. Percentages of CD44$^{hi}$/L-selectin$^{lo}$ cells are indicated. One control mouse (left) and two BAFF Tg mice (right) are shown and the results were representative of 8 animals analysed in each group.

FIG. 8 depicts ncreased B cell compartments in the spleen but not in the bone marrow of BAFF Tg mice.
(A) FACS staining for mature B cells using both anti-IgM-FITC and anti-B220-PE, in spleen (top panel), bone marrow (medium panel) and MLN (bottom panel). Percentages of B220+/IgM+mature B cells are indicated.
(B) FACS staining for preB cells (B220+/CD43−) and proB cells (B220+/CD43+) in the bone marrow using anti-CD43-FITC, anti-B220-Cy-chrome and anti-IgM-PE simultaneously. Are shown cells gated on the IgM negative population. Percentages of preB cells (B220+/CD43−) and proB cells (B220+/CD43+) cells are indicated.
For all figures (A and B) one control mouse (left) and two BAFF Tg mice (right) are shown and results are representative of 7 animals analysed for each group.

FIG. 9 depicts increased Ig, RF and CIC levels in BAFF Tg mice
(A) SDS-PAGE of two control sera (−) and 4 sera from BAFF Tg mice (+) side by side with the indicated amount of a purified mouse IgG for reference. The intensity of the albumin band in similar in all lanes indicating that the material loaded on the gel is equivalent for each sample. ELISA-based analysis of total mouse Ig (B), RF (C) and CIC (D) in the sera of 19 control littermates (white bars) and 21 BAFF Tg mice (Black bars). In the absence of a proper RF control, the titer (log base 2) for RF is defined as the dilution of the sera giving an O.D. 3 times higher than that of background. The quantity of CIC is defined as the quantity of PAP required to generate an O.D. equivalent to that obtained with the tested serum. The difference between control animals and BAFF Tg mice was statistically significant (P<0.001 in (B) and (C), P<0.003 in (D)).

FIG. 10 depicts the presence of anti-ssDNA and anti-dsDNA autoantibodies in some BAFF Tg mice.
(A) Analysis by ELISA of anti-ssDNA autoantibodies in 19 control littermates (gray bars) and 21 BAFF Tg mice (black bars).
(B) Analysis by ELISA of anti-ssDNA autoantibodies in 5 control littermates and the 5 animals showing levels of anti-ssDNA autoantibodies from (A).
(C) Paraffin sections of kidneys from a control mouse (left) and a BAFF Tg mouse (right), stained with goat anti-mouse Ig-HRP. Ig deposition is shown by a brown staining. These pictures are representative of 6 BAFF Tg mice analysed.

Figure 11:
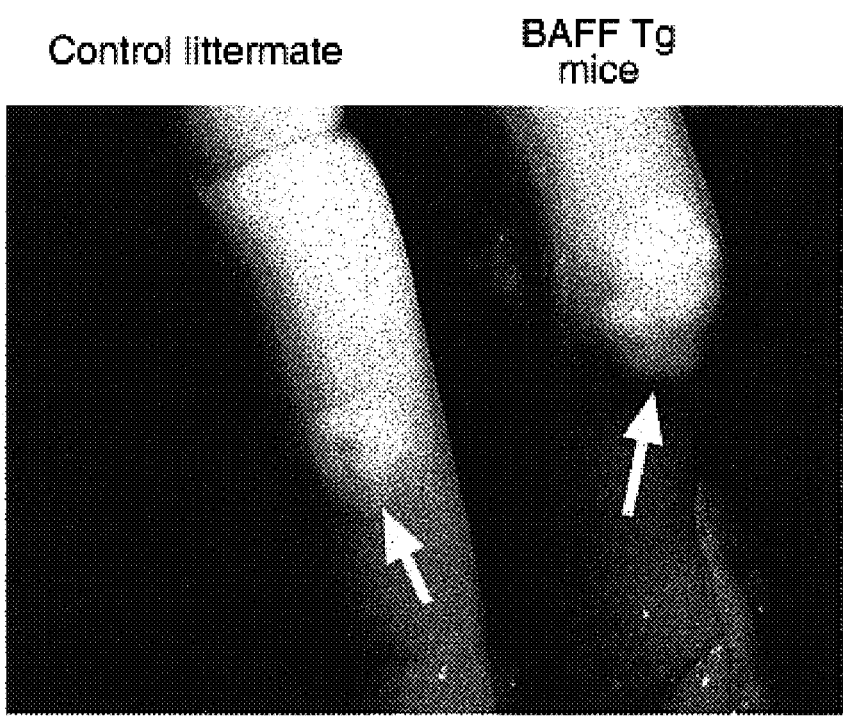

FIG. 11 depicts enlarged Peyer's patches in BAFF Tg mice.
Photography of Peyers patches (indicated with an arrow) on the small intestine of a control mouse (left) and a BAFF Tg mouse (right). This pictures is representative of at least 12 mice sacrificed for each group. Magnification 5×

Figure 12:
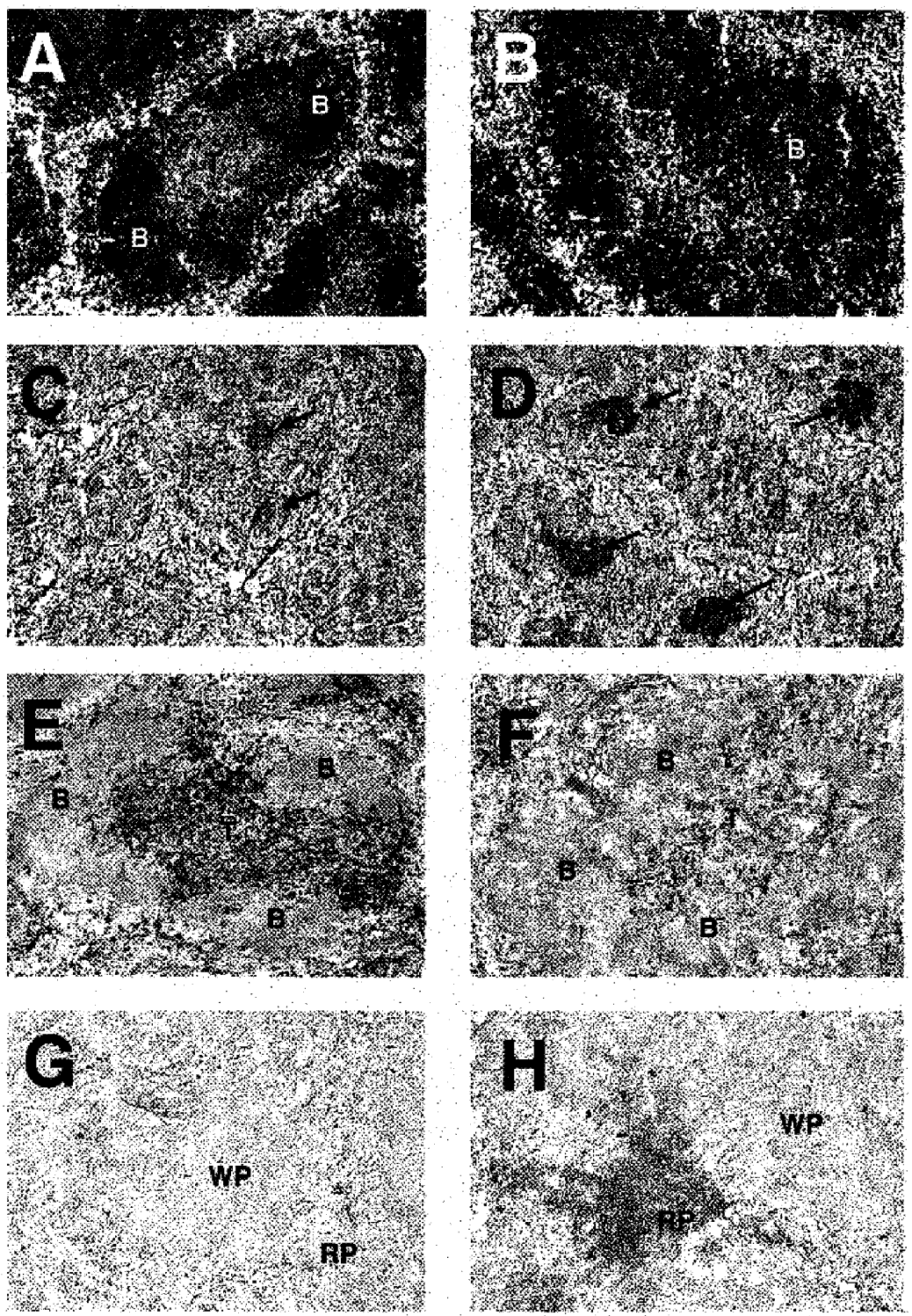

FIG. 12 depicts disrupted T and B cell organization, intense germinal center reactions, decreased number of dendritic cells and increased number of plasma cells in the spleen of BAFF Tg mice.
A control mouse is shown in A, C, E and G and a BAFF Tg in B, D, F, and H. B cells are blue and T cells brown (A and B). Germinal centers are shown with an arrow (C and D). Only few residual germinal centers are seen in control mice (C). CD11c positive dendritic cells are brown and appear in the T cell zone, bridging channels and the marginal zone (E). Very few are present in BAFF Tg mice (F). Syndecan-1- positive plasma cells were only detectable in the red pulp of BAFF Tg mice (H) but not control mice (G).

These pictures are representative of at least 12 BAFF Tg mice analysed and 12 control mice. The magnification is 100× for all pictures except C and D which are 50×.
B: B cell follicle, T: PALS, WP: white pulp, RP: red pulp.

Figure 13:
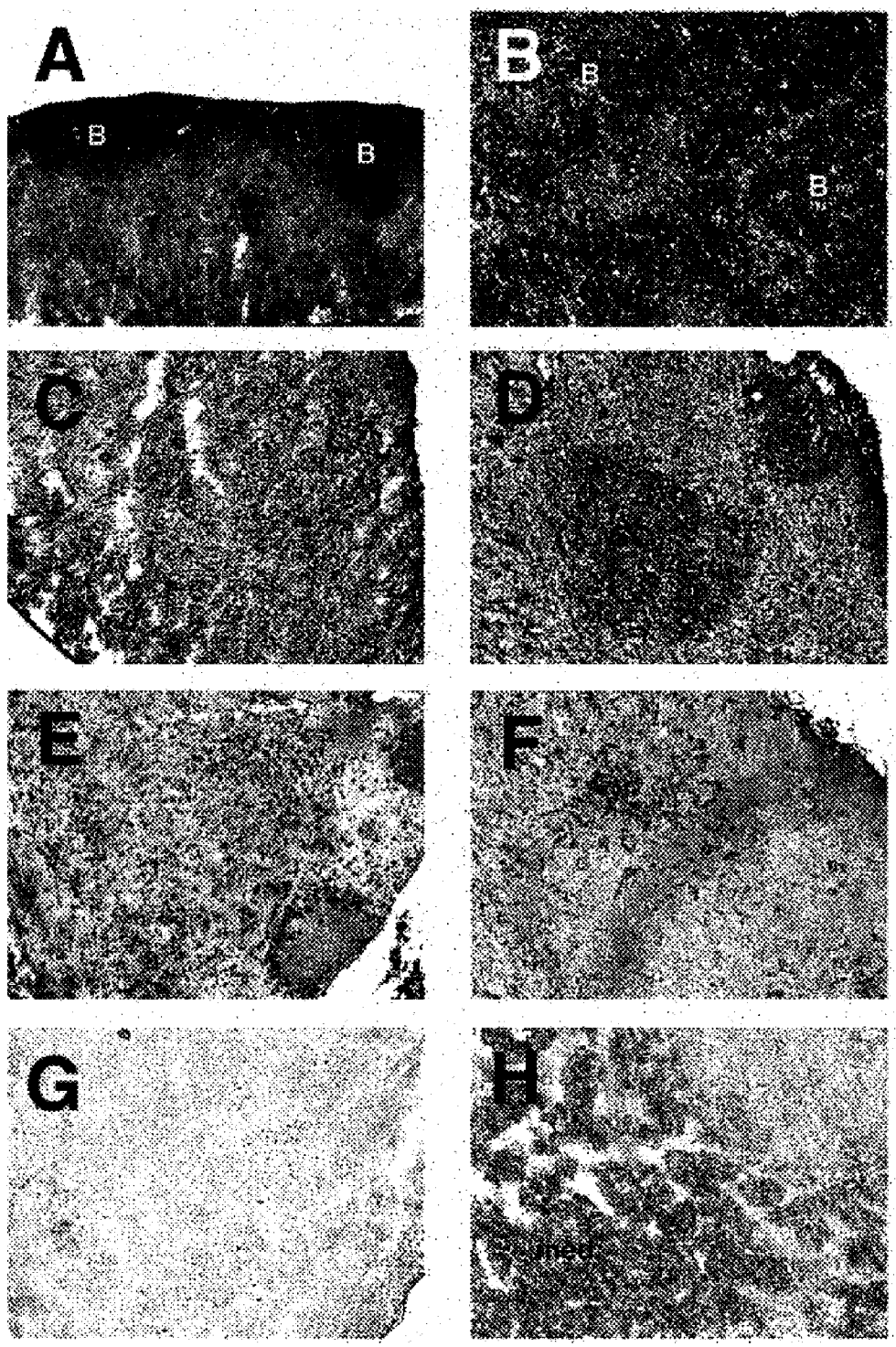

FIG. 13 depicts disrupted T and B cells organization, intense germinal center reactions and large number of plasma cells in the MLN of BAFF Tg mice.

The control mouse is shown in A, C, E and G and the BAFF Tg mouse is shown in B, D, F, and H. The immunohistochemistry was performed as described in FIG. 6. T and B cell staining is shown in A and B, germinal centers in C and D, dendritic cells E and F and plasma cells in G and H. GC: germinal center. Magnification 100×.

DETAILED DESCRIPTION OF THE INVENTION

Reference will now be made in detail to the present preferred embodiments of the invention. This invention relates to the use of BAFF and BAFF related molecules to effect the growth and maturation of B-cells and the secretion of immunoglobulin. The invention relates to the use of BAFF and BAFF related molecules to effect responses of the immune system, as necessitated by immune-related disorders. Additionally, this invention encompasses the treatment of cancer and immune disorders through the use of a BAFF, or BAFF related gene through gene therapy methods.

The BAFF ligand and homologs thereof produced by hosts transformed with the sequences of the invention, as well as native BAFF purified by the processes known in the art, or produced from known amino acid sequences, are useful in a variety of methods for anticancer, antitumor and immunoregulatory applications. They are also useful in therapy and methods directed to other diseases.

Another aspect of the invention relates to the use of the polypeptide encoded by the isolated nucleic acid encoding the BAFF-ligand in "antisense" therapy. As used herein, "antisense" therapy refers to administration or in situ generation of oligonucleotides or their derivatives which specifically hybridize under cellular conditions with the cellular mRNA and/or DNA encoding the ligand of interest, so as to inhibit expression of the encoded protein, i.e. by inhibiting transcription and/or translation. The binding may be by conventional base pair complementarity, or, for example, in the case of binding to DNA duplexes, through specific interactions in the major groove of the double helix. In general, "antisense" therapy refers to a range of techniques generally employed in the art, and includes any therapy which relies on specific binding to oligonucleotide sequences.

An antisense construct of the present invention can be delivered, for example, as an expression plasmid, which, when transcribed in the cell, produces RNA which is complementary to at least a portion of the cellular mRNA which encodes Kay-ligand. Alternatively, the antisense construct can be an oligonucleotide probe which is generated ex vivo. Such oligonucleotide probes are preferably modified oligonucleotides which are resistant to endogenous nucleases, and are therefor stable in vivo. Exemplary nucleic acids molecules for use as antisense oligonucleotides are phosphoramidates, phosphothioate and methylphosphonate analogs of DNA (See, e.g., U.S. Pat. No. 5,176,996; U.S. Pat. No. 5,264,564; and U.S. Pat. No. 5,256,775). Additionally, general approaches to constructing oligomers useful in antisense therapy have been reviewed, for example, by Van Der Krol et al., (1988) *Biotechniques* 6:958–976; and Stein et al. (1988) *Cancer Res* 48: 2659–2668, specifically incorporated herein by reference.

C. BAFF-Ligand

The BAFF-ligand of the invention, as discussed above, is a member of the TNF family and is described in PCT application number PCT/US98/19037 (WO99/12964) and is incorporated in its entirety herewith. The protein, fragments or homologs thereof may have wide therapeutic and diagnostic applications.

The BAFF-ligand is present primarily in the spleen and in peripheral blood lymphocytes, strongly indicating a regulatory role in the immune system. Comparison of the claimed BAFF-ligand sequences with other members of the human TNF family reveals considerable structural similarity. All the proteins share several regions of sequence conservation in the extracellular domain.

Although the precise three-dimensional structure of the claimed ligand is not known, it is predicted that, as a member of the TNF family, it may share certain structural characteristics with other members of the family.

The novel polypeptides of the invention specifically interact with a receptor, which has not yet been identified. However, the peptides and methods disclosed herein enable the identification of receptors which specifically interact with the BAFF-ligand or fragments thereof.

The claimed invention in certain embodiments includes methods of using peptides derived from BAFF-ligand which have the ability to bind to their receptors. Fragments of the BAFF-ligands can be produced in several ways, e.g., recombinantly, by PCR, proteolytic digestion or by chemical synthesis. Internal or terminal fragments of a polypeptide can be generated by removing one or more nucleotides from one end or both ends of a nucleic acid which encodes the polypeptide. Expression of the mutagenized DNA produces polypeptide fragments.

Polypeptide fragments can also be chemically synthesized using techniques known in the art such as conventional Merrifield solid phase f-moc or t-boc chemistry. For example, peptides and DNA sequences of the present invention may be arbitrarily divided into fragments of desired length with no overlap of the fragment, or divided into overlapping fragments of a desired length. Methods such as these are described in more detail below.

Generation of Soluble Forms of BAFF-ligand

Soluble forms of the BAFF-ligand can often signal effectively and hence can be administered as a drug which now mimics the natural membrane form. It is possible that the BAFF-ligand claimed herein are naturally secreted as soluble cytokines, however, if not, one can reengineer the gene to force secretion. To create a soluble secreted form of BAFF-ligand, one would remove at the DNA level the N-terminus transmembrane regions, and some portion of the stalk region, and replace them with a type leader or alternatively a type II leader sequence that will allow efficient proteolytic cleavage in the chosen expression system. A skilled artisan could vary the amount of the stalk region retained in the secretion expression construct to optimize both receptor binding properties and secretion efficiency. For example, the constructs containing all possible stalk lengths, i.e. N-terminal truncations, could be prepared such that proteins starting at amino acids 81 to 139 would result. The optimal length stalk sequence would result from this type of analysis.

E. Generation of Antibodies Reactive with the BAFF-ligand

The invention also includes antibodies specifically reactive with the claimed BAFF-ligand or its receptors. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers, or other techniques, well known in the art.

An immunogenic portion of BAFF-ligand or its receptors can be administered in the presence of an adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of BAFF-ligand or its receptors, (e.g. antigenic determinants of a polypeptide of SEQ. ID. NO.: 2, said sequence as described in PCT application number PCT/US98/19037 (WO99/12964) and is incorporated in its entirety herewith), or a closely related human or non-human mammalian homolog (e.g. 70, 80 or 90 percent homologous, more preferably at least 95 percent homologous). In yet a further preferred embodiment of the present invention, the anti-BAFF-ligand or anti-BAFF-ligand-receptor antibodies do not substantially cross react (i.e. react specifically) with a protein which is e.g., less than 80 percent homologous to SEQ. ID. NO.: 2 or 6 said sequence as described in PCT application number PCT/US98/19037 (WO99/12964) and is incorporated in its entirety herewith; preferably less than 90 percent homologous with SEQ. ID. NO.: 2 said sequence as described in PCT application number PCT/US98/19037 (WO99/12964) and is incorporated in its entirety herewith; and, most preferably less than 95 percent homologous with SEQ. ID. NO.: 2 said sequence as described in PCT application number PCT/US98/19037 (WO99/12964) and is incorporated in its entirety herewith. By "not substantially cross react", it is meant that the antibody has a binding affinity for a non-homologous protein which is less than 10 percent, more preferably less than 5 percent, and even more preferably less than 1 percent, of the binding affinity for a protein of SEQ. ID. NO.: 2 said sequence as described in PCT application number PCT/US98/19037 (WO99/12964) and is incorporated in its entirety herewith.

The term antibody as used herein is intended to include fragments thereof which are also specifically reactive with BAFF-ligand, or its receptors. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibodies of the present invention are further intended to include biospecific and chimeric molecules having anti-BAFF-ligand or anti-BAFF-ligand-receptor activity. Thus, both monoclonal and polyclonal antibodies (Ab) directed against BAFF-ligand, Tumor-ligand and their receptors, and antibody fragments such as Fab' and F(ab')$_2$, can be used to block the action of the Ligand and their respective receptor.

Various forms of antibodies can also be made using standard recombinant DNA techniques. Winter and Milstein (1991) *Nature* 349: 293–299, specifically incorporated by reference herein. For example, chimeric antibodies can be constructed in which the antigen binding domain from an animal antibody is linked to a human constant domain (e.g. Cabilly et al., U.S. Pat. No. 4,816,567, incorporated herein by reference). Chimeric antibodies may reduce the observed immunogenic responses elicited by animal antibodies when used in human clinical treatments.

In addition, recombinant "humanized antibodies" which recognize BAFF-ligand or its receptors can be synthesized. Humanized antibodies are chimeras comprising mostly human IgG sequences into which the regions responsible for specific antigen-binding have been inserted. Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (i.e. inter species) sequences in human antibodies, and thus are less likely to elicit immune responses in the treated subject.

Construction of different classes of recombinant antibodies can also be accomplished by making chimeric or humanized antibodies comprising variable domains and human constant domains (CH1, CH2, CH3) isolated from different classes of immunoglobulins. For example, antibodies with increased antigen binding site valencies can be recombinantly produced by cloning the antigen binding site into vectors carrying the human: chain constant regions. Arulanandam et al. (1993) *J. Exp. Med.*, 177: 1439–1450, incorporated herein by reference.

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling. Queen et al., (1989) *Proc. Natl. Acad. Sci.* 86: 10029–33 incorporated herein by reference.

F. Generation of Analogs: Production of Altered DNA and Peptide Sequences

Analogs of the BAFF-ligand can differ from the naturally occurring BAFF-ligand in amino acid sequence, or in ways that do not involve sequence, or both. Non-sequence modifications include in vivo or in vitro chemical derivatization of the BAFF-ligand. Non-sequence modifications include, but are not limited to, changes in acetylation, methylation, phosphorylation, carboxylation or glycosylation.

Preferred analogs include BAFF-ligand biologically active fragments thereof, whose sequences differ from the sequence given in SEQ. ID NO. 2 said sequence as described in PCT application number PCT/US98/19037 (WO99/12964) and is incorporated in its entirety herewith, by one or more conservative amino acid substitutions, or by one or more non-conservative amino acid substitutions, deletions or insertions which do not abolish the activity of BAFF-ligand. Conservative substitutions typically include the substitution of one amino acid for another with similar characteristics, e.g. substitutions within the following groups: valine, glycine; glycine, alanine; valine, isoleucine, leucine; aspartic acid, glutamic acid; asparagine, glutamine; serine, threonine; lysine, arginine; and, phenylalanine, tyrosine.

G. Materials and Methods of the Invention

The anti-Flag M2 monoclonal antibody, biotinylated anti-Flag M2 antibody and the anti-Flag M2 antibody coupled to agarose were purchased from Sigma. Cell culture reagents were obtained from Life Sciences (Basel, Switzerland) and Biowhittaker (Walkersville, Md.). Flag-tagged soluble human APRIL (residues $K_{110}$-$L_{250}$) was produced in 293 cells as described (10, 11). FITC-labeled anti-CD4, anti-CD8 and anti-CD19 antibodies were purchased from Pharmingen (San Diego, Calif.). Goat F(ab)$_2$ specific for the Fc$_5\mu$ fragment of human IgM were purchased from Jackson ImmunoResearch (West Grove, Pa.). Secondary antibodies were obtained from either Pharmingen or from Jackson ImmunoResearch and used at the recommended dilutions.

Human embryonic kidney 293 T (12) cells and fibroblast cell lines (Table 1) were maintained in DMEM containing 10% heat-inactivated fetal calf serum (FCS). Human embryonic kidney 293 cells were maintained in DMEM-nutrient mix F12 (1:1) supplemented with 2% FCS. T cell lines, B cell lines, and macrophage cell lines (Table 1) were grown in RPMI supplemented with 10% FCS. Molt-4 cells were cultivated in Iscove's medium supplemented with 10% FCS. Epithelial cell lines were grown in MEM-alpha medium containing 10% FCS, 0.5 mM non-essential amino acids, 10 mM Na-Hepes and 1 mM Na pyruvate. HUVECs were maintained in M199 medium supplemented with 20% FCS, 100 µg/ml of epithelial cell growth factor (Collaborative Research, Inotech, Dottikon, Switzerland) and 100 µg/ml of heparin sodium salt (Sigma). All media contained penicillin and streptomycin antibiotics. Peripheral blood leukocytes were isolated from heparinized blood of healthy adult volunteers by Ficoll-Paque (Pharmacia, Uppsala, Sweden) gradient centrifugation and cultured in RPMI, 10% FCS.

T cells were obtained from non-adherents PBLs by rosetting with neuraminidase-treated sheep red blood cells and separated from non-rosetting cells (mostly B cells and monocytes) by Ficoll-Paque gradient centrifugation. Purified T cells were activated for 24 h with phytohemagglutinin (Sigma) (1 µg/ml), washed and cultured in RPMI, 10% FCS, 20 U/ml of IL-2. CD14$^+$ monocytes were purified by magnetic cell sorting using anti-CD14 antibodies, goat anti-mouse-coated microbeads and a Minimacs™ device (Miltenyi Biotech), and cultivated in the presence of GM-CSF (800 U/ml, Leucomax®, Essex Chemie, Luzern, Switzerland) and IL-4 (20 ng/ml, Lucerna Chem, Luzern, Switzerland) for 5 d, then with GM-CSF, IL-4 and TNFα (200 U/ml, Bender, Vienna, Austria) for an additional 3 d to obtain a CD83$^+$, dentritic cell-like population. Human B cells of >97% purity were isolated from peripheral blood or umbilical cord blood using anti-CD 19 magnetic beads (M450, Dynal, Oslo, Norway) as described (13).

Northern Blot Analysis

Northern blot analysis was carried out using Human Multiple Tissue Northern Blots I and II (Clontech #7760-1 and #7759-1). The membranes were incubated in hybridization solution (50% formamide, 2.5× Denhardt's, 0.2% SDS, 10 mM EDTA, 2× SSC, 50 mM NaH$_2$PO$_4$, pH 6.5, 200 µg/ml sonicated salmon sperm DNA) for 2 h at 60° C. Antisense RNA probe containing the nucleotides corresponding to amino acids 136–285 of hBAFF was heat-denatured and added at 2×10$^6$ cpn/ml in fresh hybridization solution. The membrane was hybridized 16 h at 62° C., washed once in 2× SSC, 0.05% SDS (30 min at 25° C.), once in 0.1× SSC, 0.1% SDS (20 min at 65° C.) and exposed 70° C. to X-ray films.

Characterization of BAFF cDNA.

A partial sequence of human BAFF cDNA was contained in several EST clones (e.g. GenBank Accession numbers T87299 and AA166695) derived from fetal liver and spleen and ovarian cancer libraries. The 5' portion of the cDNA was obtained by 5'-RACE-PCR (Marathon-Ready cDNA, Clonetech, Palo Alto, Calif.) amplification with oligonucleotides AP1 and JT1013 (5'-ACTGTTTCTTCTGGACCCTGAACGGC-3') [SEQ ID. NO.: 9] using the provided cDNA library from a pool of human leukocytes as template, as recommended by the manufacturer. The resulting PCR product was cloned into PCR-0 blunt (Invitrogen, NV Leek, The Netherlands) and subcloned as EcoRI/PstI fragment into pT7T3 Pac vector (Pharmacia) containing EST clone T87299. Full-length hBAFF cDNA was therefore obtained by combining 5' and 3' fragments using the internal PstI site of BAFF. Sequence has been assigned GenBank accession number AF116456.

A partial 617 bp sequence of murine BAFF was contained in two overlapping EST clones (AA422749 and AA254047). A PCR fragment spanning nucleotides 158 to 391 of this sequence was used as a probe to screen a mouse spleen cDNA library (Stratagene, La Jolla, Calif.).

Expression of Recombinant BAFF

Full length hBAFF was amplified using oligos JT1069 (5'-GACAAGCTTGCCACCATGGATGACTCCACA-3') [SEQ. ID. NO.: 10] and JT637 (5'-ACTAGTCACAGCAGTTTCAATGC-3') [SEQ. ID. NO.: 11]. The PCR product was cloned into PCR-0 blunt and re-subcloned as HindIII/EcoRI fragment into PCR-3 mammalian expression vector. A short version of soluble BAFF (amino acids Q136-L285) was amplified using oligos JT636 (5'-CTGCAGGGTCCAGAAGAAACAG-3') [SEQ. ID. NO.: 12] and JT637. A long version of soluble BAFF (aa L83-L285) was obtained from full length BAFF using internal PstI site. Soluble BAFFs were resubcloned as PstI/EcoRI fragments behind the haemaglutinin signal peptide and Flag sequence of a modified PCR-3 vector, and as PstI/SpeI fragments into a modified pQE16 bacterial expression vector in frame with a N-terminal Flag sequence (14). Constructs were sequenced on both strands. The establishment of stable 293 cell lines expressing the short soluble form or full length BAFF, and the expression and purification of recombinant soluble BAFF from bacteria and mammalian 293 cells was performed as described (14, 15).

Reverse Transcriptase PCR

Total RNA extracted from T cells, B cells, in vitro derived immature dendritic cells, 293 wt and 293-BAFF (full length) cells was reverse transcribed using the Ready to Go system (Pharmacia) according to the manufacturer's instructions. BAFF and β-actin cDNAs were detected by PCR amplification with Taq DNA polymerase (steps of 1 min each at 94° C., 55° C. and 72° C. for 30 cycles) using specific oligonucleotides: for BAFF, JT1322 5'-GGAGAAGGC AACTCCAGTCAGAAC-3' [SEQ. ID. NO.: 13] and JT1323 5'-CAATTCATCCCCAAAGACATGGAC-3' [SEQ. ID. NO.: 14]; for IL-2 receptor alpha chain, JT1368 5'-TCGGAACACAACGAAACAAGTC-3' [SEQ. ID. NO.: 15] and JT1369 5'-CTTCTCCTTCACCTGGA AACTGACTG-3' [SEQ. ID NO.: 16]; for β-actin, 5'-GGCATCGTGATGGACTCCG-3' [SEQ. ID. NO.: 17] and 5'-GCTGGAAGGTGGACAGCGA-3' [SEQ. ID. NO.: 18].

Gel Permeation Chromatography 293T cells were transiently transfected with the short form of soluble BAFF and grown in serum-free Optimem medium for 7 d. Conditionned supernatants were concentrated 20×, mixed with internal standards catalase and ovalbumin, and loaded onto a Superdex-200 HR10/30 column. Proteins were eluted in PBS at 0.5 ml/min and fractions (0.25 ml) were precipitated with trichloroacetic acid and analyzed by Western blotting using anti-Flag M2 antibody. The column was calibrated with standard proteins: ferritin (440 kDa), catalase (232 kDa), aldolase (158 kDa), bovine serum albumine (67 kDa), ovalbumine (43 kDa), chymotrypsinogen A (25 kDa) and ribonuclease A (13.7 kDa).

PNGase F Treatment

Samples were heated in 20 $\mu$l of 0.5% SDS, 1% 2-mercaptoethanol for 3 min at 95° C., then cooled and supplemented with 10% Nonidet P-40 (2 $\mu$l), 0.5 M sodium phosphate, pH 7.5 (2 $\mu$l) and Peptide N-glycanase F (125 units/$\mu$l, 1 $\mu$l, or no enzyme in controls). Samples were incubated for 3 h at 37° C. prior to analysis by Western blotting.

EDMAN Sequencing

293 T cells were transiently transfected with the long form of soluble BAFF and grown in serum-free Optimem medium for 7 d. Conditioned supernatants were concentrated 20×, fractionated by SDS-PAGE and blotted onto polyvinylidene difluoride membrane (BioRad Labs, Hercules, Calif.) as previously described (16), and then sequenced using a gas phase sequencer (ABI 120A, Perkin Elmer, Foster City, Calif.) coupled to an analyzer (ABI 120A, Perkin Elmer) equipped with a phenylthiohydantoin C18 2.1×250 mm column. Data was analyzed using software ABI 610 (Perkin Elmer).

Antibodies

Polyclonal antibodies were generated by immunizing rabbits (Eurogentec, Seraing, Belgium) with recombinant soluble BAFF. Spleen of rats immunized with the same antigen were fused to x63Ag8.653 mouse myeloma cells, and hybridoma were screened for BAFF-specific IgGs. One of these monoclonal antibodies, 43.9, is an IgG2a that specifically recognizes hBAFF.

Cells were stained in 50 $\mu$l of FACS buffer (PBS, 10% FCS, 0.02% NaN$_3$) with 50 ng (or the indicated amount) of Flag tagged short soluble hBAFF for 20 min at 4° C., followed by anti-Flag M2 (1 $\mu$g) and secondary antibody. Anti-BAFF mAb 43.9 was used at 40 $\mu$g/ml. For two color FACS analysis, peripheral blood lymphocytes were stained with Flag tagged soluble BAFF/long (2 $\mu$g/ml), followed by biotinylated anti-Flag M2 (1/400) and PE-labeled streptavidin (1/100), followed by either FITC-labeled anti-CD4, anti-CD8 or anti-CD19.

PBL Proliferation Assay

Peripheral blood leukocytes were incubated in 96-well plates (10$^5$ cells/well in 100 $\mu$l RPMI supplemented with 10% FCS) for 72 h in the presence or absence of 2 $\mu$g/ml of goat anti-human $\mu$ chain antibody (Sigma) or control F(ab')$_2$ and with the indicated concentration of native or boiled soluble BAFF/long. Cells were pulsed for an additional 6 h with [$^3$H]thymidine (1 $\mu$Ci/well) and harvested. [$^3$H] thymidine incorporation was monitored by liquid scintillation counting. In some experiments, recombinant soluble BAFF was replaced by 293 cells stably transfected with full length BAFF (or 293 wt as control) that had been fixed for 5 min at 25° C. in 1% paraformaldeyde. Assay was performed as described (17). In further experiments, CD 19$^+$ cells were isolated form PBL with magnetic beads and the remaining CD19$^-$ cells were irradiated (3000 rads) prior to renconstitution with CD19$^+$ cells. Proliferation assay with sBAFF was then performed as described above.

B Cell Activation Assay

Purified B cells were activated in the EL-4 culture system as described (13). Briefly, 10$^4$ B cells mixed with 5×10$^4$ irradiated murine EL-4 thymoma cells (clone B5) were cultured for 5–6 d in 200 $\mu$l medium containing 5% v/v of culture supernatants from human T cells (10$^6$/ml) which had been activated for 48 h with PHA (1 $\mu$g/ml) and PMA (1 ng/ml). B cells were then reisolated with anti-CD19 beads and cultured for another 7 d (5×10$^4$ cells in 200 $\mu$l, duplicate or triplicate culture in flat bottomed 96 well plates) in medium alone or in medium supplemented with 5% T cell supernatants, or with 50 ng/ml IL-2 (a kind gift from the former Glaxo Institute for Molecular Biology, Geneva) and 10 ng/ml each IL-4 and IL-10 (Peprotech, London, UK), in the presence or absence of sBAFF. The anti-Flag M2 antibody was added at a concentration of 2 $\mu$g/ml and had no effect by itself. IgM, IgG and IgA in culture supernatants were quantitated by ELISA assays as described (13).

Human BAFF was identified by sequence homology as a possible novel member of the TNF ligand family while we screened public databases using an improved profile search (18). A cDNA encoding the complete protein of 285 amino acids (aa) was obtained by combining EST-clones (covering the 3' region) with a fragment (5' region) amplified by PCR. The absence of a signal peptide suggested that BAFF was a type II membrane protein that is typical of the members of the TNF-ligand family. The protein has a predicted cytoplasmic domain of 46 aa, a hydrophobic transmembrane region, and an extracellular domain of 218 aa containing two potential N-glycosylation sites (FIG. 1A). The sequence of the extracellular domain of BAFF shows highest homology with APRIL (33% amino acid identities, 48% homology), whereas the identity with other members of the family such as TNF, FasL, LTα, TRAIL or RANKL is below 20% (FIGS. 1B, C). The mouse BAFF cDNA clone isolated from a spleen library encoded a slightly longer protein (309 aa) due to an insertion between the transmembrane region and the first of several β-strands which constitute the receptor binding domain in all TNF ligand members (19). This β-strand rich ectodomain is almost identical in mouse and human BAFF (86% identity, 93% homology) suggesting that the BAFF gene has been highly conserved during evolution (FIG. 1A).

Figure 2A:
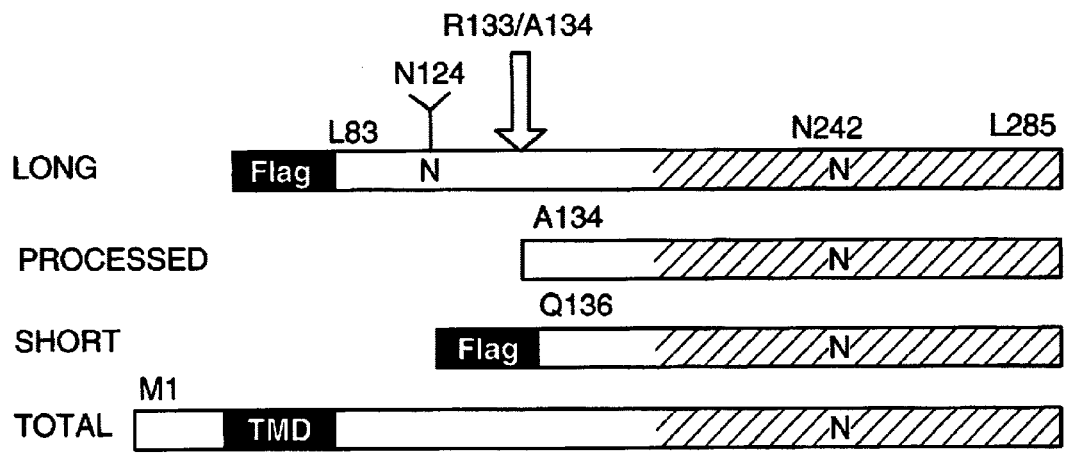
FIG. 2 is a schematic characterization of recombinant BAFF (A) Schematic representation of recombinant BAFF constructs. Soluble recombinant BAFFs starting at $Leu_{83}$ and $Gln_{136}$ are expressed fused to a N-terminal Flag tag and a 6 amino acid linker. The long form is cleaved between $Arg_{133}$ and $Ala_{134}$ (arrow) in 293 T cells, to yield a processed form of BAFF. $Asn_{124}$ and $Asn_{242}$ belong to N-glycosylation consensus sites. N-linked glycan present on $Asn_{124}$ is shown as a Y. TMD: transmembrane domain. (B) Peptide N-glycanase F (PNGase F) treatment of recombinant BAFF. Concentrated supernatants containing Flag-tagged BAFFs and APRIL were deglycosylated and analyzed by Western blotting using polyclonal anti-BAFF antibodies or anti-Flag M2, as indicated. All bands except processed BAFF also reacted with anti-Flag M2 (data not shown). (C) Full length BAFF is processed to a soluble form. 293T cells were transiently transfected with full length BAFF. Transfected cells and their concentrated supernatants were analyzed by Western blotting using polyclonal anti-BAFF antibodies. Supernatants corresponding to 10× the amount of cells were loaded onto the gel. (D) Size exclusion chromatography of soluble BAFF on Superdex-200. Concentrated supernatants containing soluble BAFF/short were fractionated on a Superdex-200 column and the eluted fractions analyzed by Western blotting using anti-Flag M2 antibody. The migration positions of the molecular mass markers (in kDa) are indicated on the left-hand side for SDS-PAGE and at the top of the figure for size exclusion chromatography.
Figure 2B:
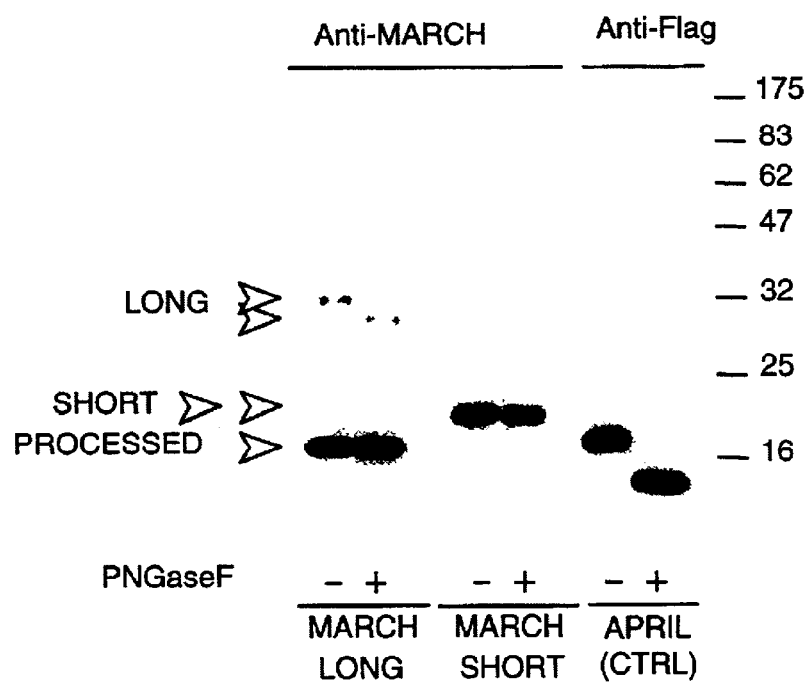

Although TNF family members are synthesized as membrane inserted ligands, cleavage in the stalk region between transmembrane and receptor binding domain is frequently observed. For example, TNF or FasL are readily cleaved from the cell surface by metalloproteinases (20, 21). While producing several forms of recombinant BAFF in 293T cells, we noticed that a recombinant soluble 32 kDa form of BAFF (aa 83-285, sBAFF/long), containing the complete stalk region and a N-terminal Flag-tag in addition to the receptor binding domain, was extensively processed to a smaller 18 kDa fragment (FIGS. 2A, B). Cleavage occurred in the stalk region since the fragment was detectable only with antibodies raised against the complete receptor interaction domain of BAFF but not with anti-Flag antibodies (data not shown). Also revealed was that only N124 (located in the stalk) but not N242 (located at the entry of the F-□ sheet) was glycosylated, since the molecular mass of the non-processed sBAFF/long was reduced from 32 kDa to 30 kDa upon removal of the N-linked carbohydrates with PNGase F whereas the 18 kDa cleaved form was insensitive to this treatment. Peptide sequence analysis of the 18 kDa fragment indeed showed that cleavage occurred between R133 and A134 (FIG. 1A). R133 lies at the end of a polybasic region which is conserved between human (R-N-

Figure 2C:
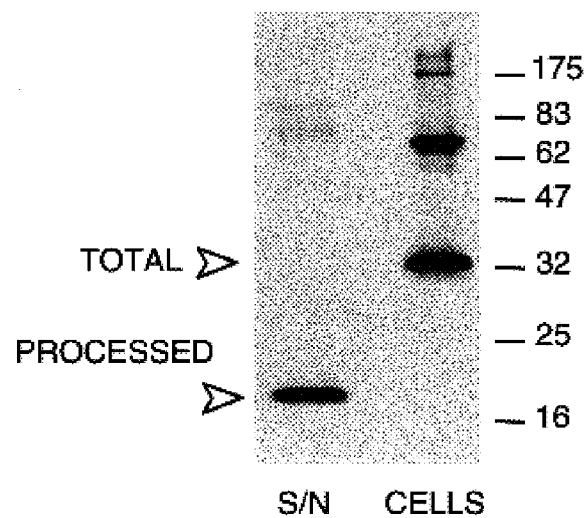

K-R) and mouse (R-N-R-R). To test whether cleavage was not merely an artifact of expressing soluble, non-natural forms of BAFF, membrane-bound full length BAFF was expressed in 293T cells (FIG. 2C). The 32 kDa complete BAFF and some higher molecular mass species (probably corresponding to non-dissociated dimers and trimers) were readily detectable in cellular extracts, but more than 95% of BAFF recovered from the supernatant corresponded to the processed 18 kDa form, indicating that BAFF was also processed when synthesized as a membrane-bound ligand.

Figure 2D:
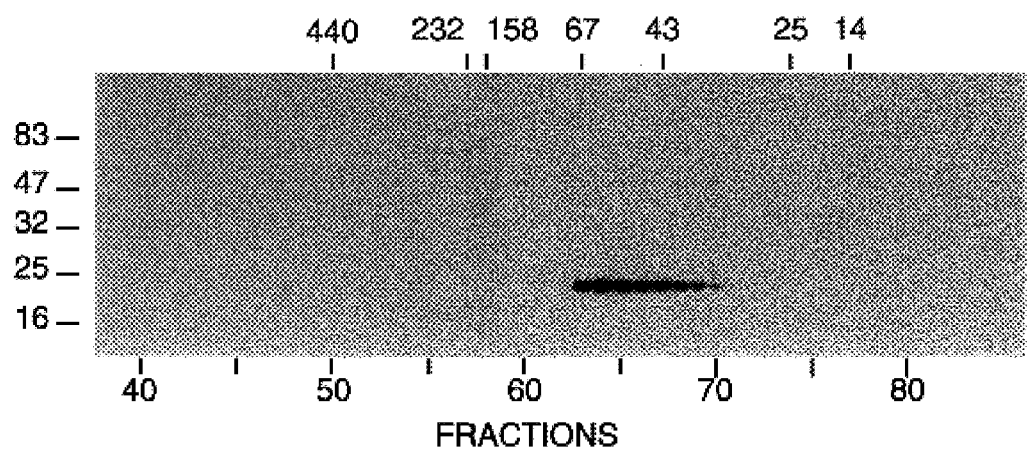

A soluble BAFF was engineered (Q136-L285, sBAFF/short) whose sequence started 2 aa downstream of the processing site (FIG. 1B). As predicted, the Flag-tag attached to the N-terminus of this recombinant molecule was not removed (data not shown) which allowed its purification by an anti-Flag affinity column. To test its correct folding, the purified sBAFF/short was analyzed by gel filtration where the protein eluted at an apparent molecular mass of 55 kDa (FIG. 2D). The sBAFF/short correctly assembles into a homotrimer (3×20 kDa) in agreement with the quaternary structure of other TNF family members (19). Finally, unprocessed sBAFF/long was readily expressed in bacteria, indicating that the cleavage event was specific to eukaryotic cells.

Figure 3A:
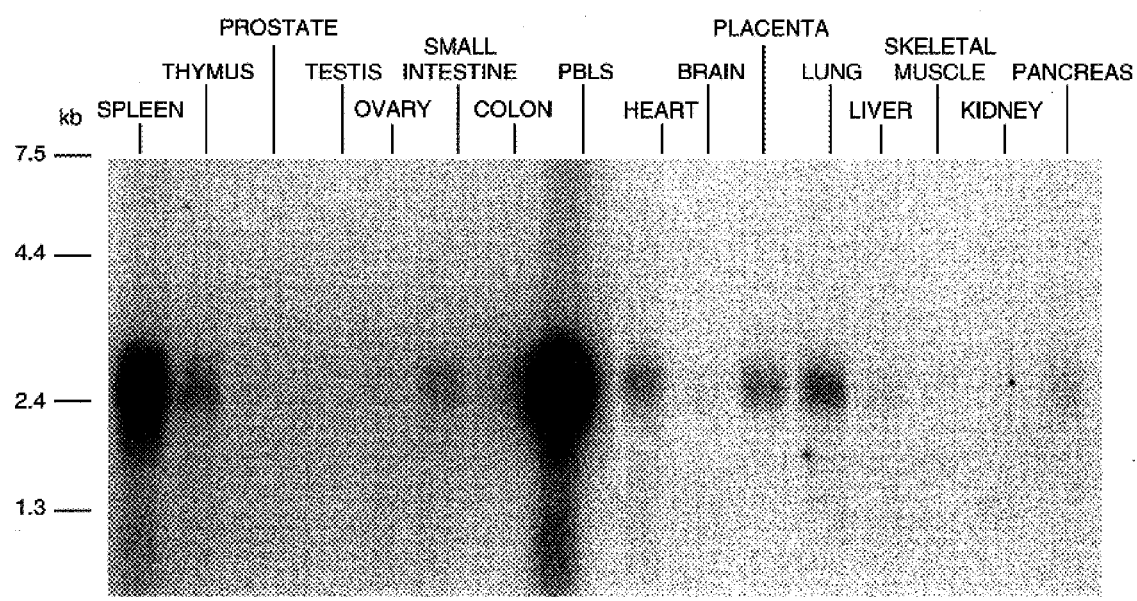
FIG. 3 depicts expression of BAFF (A) Northern blots (2 μg poly A⁺ RNA per lane) of various human tissues were probed with BAFF antisense mRNA. (B) Reverse transcriptase amplification of BAFF, IL-2 receptor alpha chain and actin from RNA of purified blood T cells at various time points of PHA activation, E-rosetting negative blood cells (B cells and monocytes), in vitro derived immature dendritic cells, 293 cells, and 293 cells sterilely transfected with full length BAFF (293-BAFF). Control amplifications were performed in the absence of added cDNA. IL-2 receptor alpha chain was amplified as a marker of T cell activation.
Figure 3B:
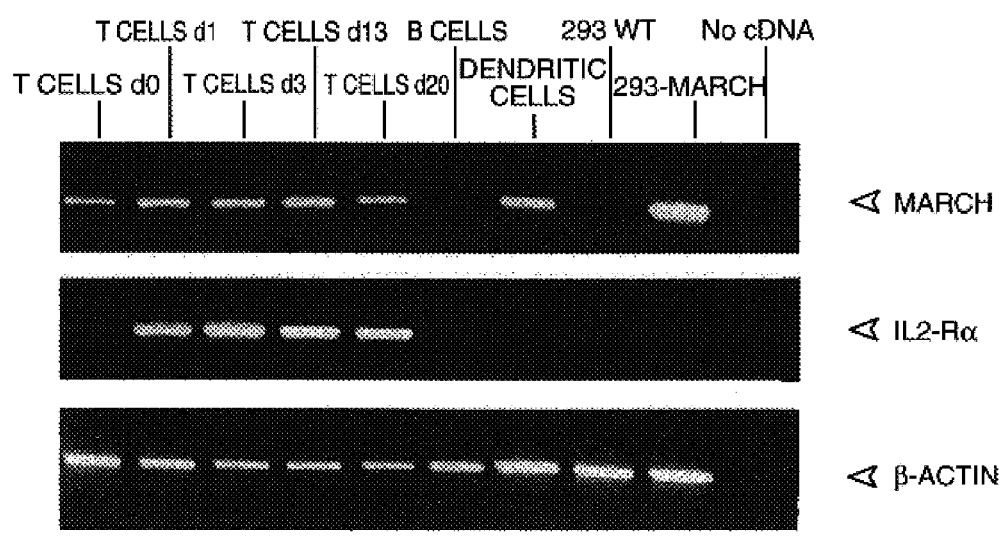

Northern blot analysis of BAFF revealed that the 2.5 kb BAFF mRNA was abundant in the spleen and PBLs (FIG. 3A). Thymus, heart, placenta, small intestine and lung showed weak expression. This restricted distribution suggested that cells present in lymphoid tissues were the main source of BAFF. Through PCR analysis, we found that BAFF mRNA was present in T cells and peripheral blood monocyte-derived dendritic cells but not in B cells (FIG. 3B). Even naive, non-stimulated T cells appeared to express some BAFF mRNA.

A sequence tagged site (STS, SHGC-36171) was found in the database which included the human BAFF sequence. This site maps to human chromosome 13, in a 9 cM interval between the markers D13S286 und D13S1315. On the cytogenetic map, this interval corresponds to 13q32-34. Of the known TNF ligand family members, only RANKL (Trance) has been localized to this chromosome (22) though quite distant to BAFF (13q14).

Figure 4A:
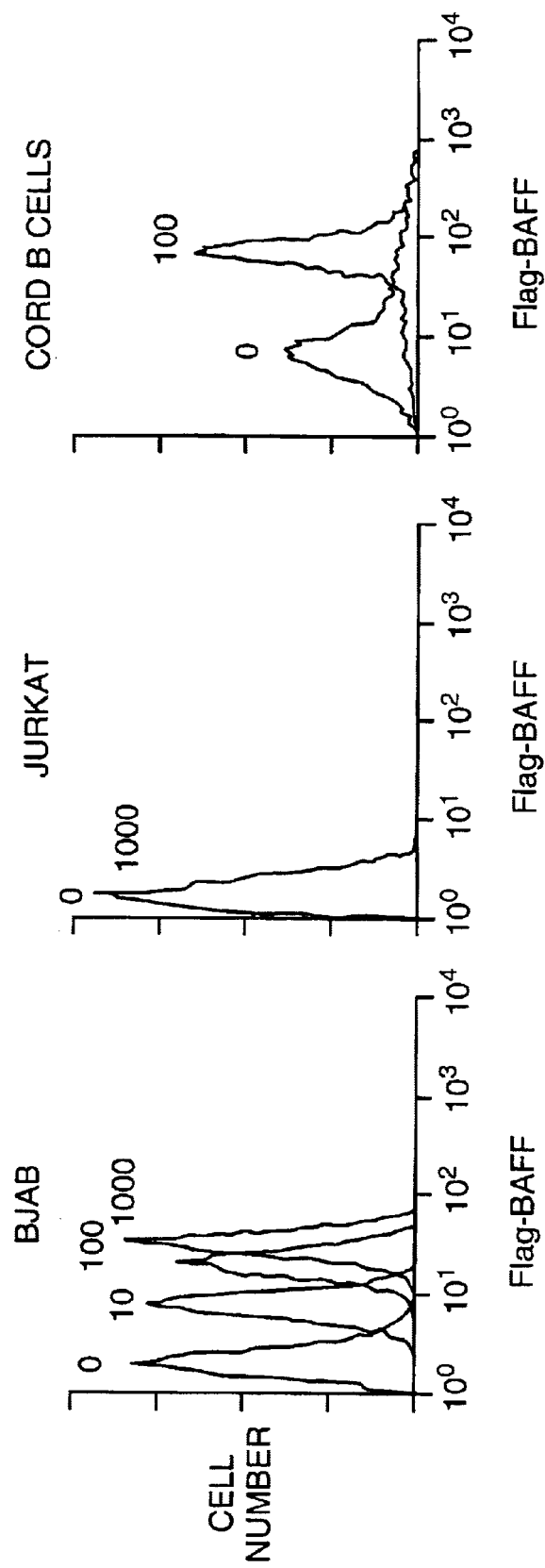
FIG. 4 depicts BAFF binding to mature B cells. (A) Binding of soluble BAFF to BJAB and Jurkat cell lines, and to purified CD19⁺ cells of cord blood. Cells were stained with the indicated amount (in ng/50 μl) of Flag-BAFF and analyzed by flow cytometry. (B) Binding of soluble BAFF to PBLs. PBLs were stained with anti-CD8-FITC or with anti-CD19-FITC (horizontal axis) and with Flag-BAFF plus M2-biotin and avidin-PE (vertical axis). Flag-BAFF was omitted in controls.
Figure 4B:
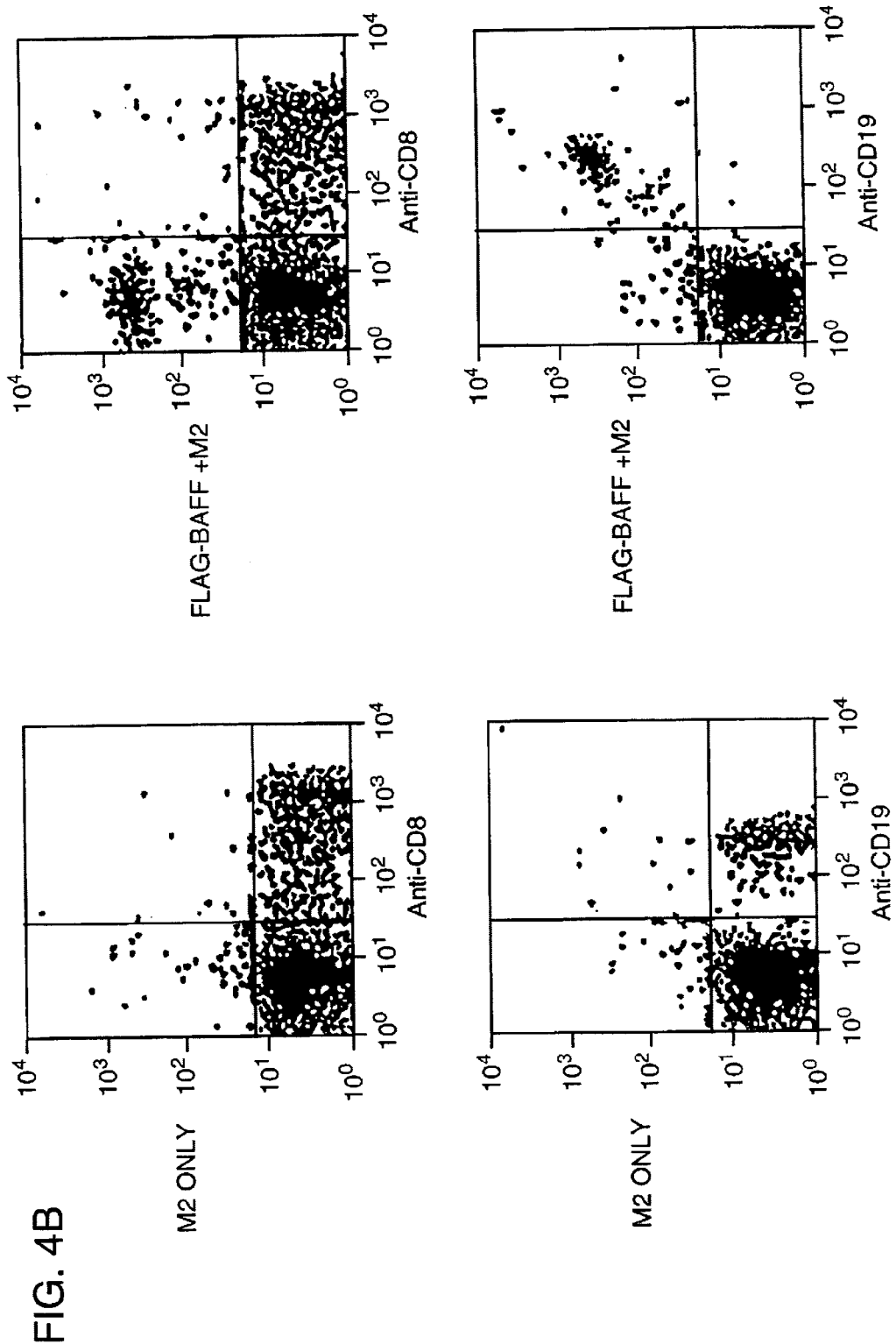

In order for the ligand to exert maximal biological effects, it was likely that the BAFF receptor (BAFF-R) would be expressed either on the same cells or on neighboring cells present in lymphoid tissues. Using the recombinant sBAFF as a tool to specifically determine BAFF-R expression by FACS, we indeed found high levels of receptor expression in various B cell lines such as the Burkitt lymphomas Raji and BJAB (FIG. 4A, Table 1). In contrast, cell lines of T cell, fibroblastic, epithelial and endothelial origin were all negative. Very weak staining was observed with the monocyte line THP-1 which, however, could be due to Fc receptor binding. Thus, BAFF-R expression appears to be restricted to B cell lines. The two mouse B cell lines tested were negative using the human BAFF as a probe, although weak binding was observed on mouse splenocytes (data not shown). The presence of BAFF-R on B cells was corroborated by analysis of umbilical cord and peripheral blood lymphocytes. While CD8$^+$ and CD4$^+$ T cells lacked BAFF-R (FIG. 4B and data not shown), abundant staining was observed on CD19$^+$ B cells (FIGS. 4A and 4B), indicating that BAFF-R is expressed on all blood B cells, including naive and memory ones.

Since BAFF bound to blood-derived B cells, experiments were performed to determine whether the ligand could deliver growth-stimulatory inhibitory signals. Peripheral blood lymphocytes (PBL) were stimulated with anti-IgM ($\mu$) antibodies together with fixed 293 cells stably expressing surface BAFF (FIG. 5A). The levels of [$^3$H]thymidine incorporation induced by anti-$\mu$ alone was not altered by the presence of control cells but was increased two-fold in the presence of BAFF-transfected cells (FIG. 5B). A dose-dependent proliferation of PBL was also obtained when BAFF-transfected cells were replaced by purified sBAFF (FIG. 5C), indicating that BAFF does not require membrane attachment to exert its activity. In this experimental setup, proliferation induced by sCD40L required concentrations exceeding 1 $\mu$g/ml but was less dependent on the presence of anti-$\mu$ than that mediated by BAFF (FIG. 5D). When purified CD19$^+$ B cells were co-cultured with irradiated autologous CD19$^-$ PBL, costimulation of proliferation by BAFF was unaffected, demonstrating that [$^3$H]thymidine uptake was mainly due to B cell proliferation and not to an indirect stimulation of another cell type (data not shown). The observed B cell proliferation in response to BAFF was entirely dependent on the presence of anti-$\mu$ antibodies, indicating that BAFF functioned as costimulator of B cell proliferation.

To investigate a possible effect of BAFF on immunoglobulin secretion, purified peripheral or cord blood B cells were preactivated by coculture with EL-4 T cells in the presence of a cytokine mixture from supernatants of PHA/PMA stimulated T cells (23). These B cells were reisolated to 98% purity and yielded a two-fold increase in Ig secretion during a secondary culture in the presence of BAFF and activated T cell cytokines as compared to cytokines alone. A very modest effect occurred in the absence of exogenous cytokines, and an intermediate (1.5-fold) effect was observed in the presence of the recombinant cytokines IL-2, IL-4 and IL-10 (FIGS. 5E, F).

The biochemical analysis of BAFF is also consistent with the typical homotrimeric structure of TNF family members. Among this family of ligands, BAFF exhibits the highest level of sequence similarity with APRIL which we have recently characterized as a ligand stimulating growth of various tumor cells (11). Unlike TNF and LT□ which are two family members with equally high homology (33% identity) and whose genes are linked on chromosome 6, APRIL and BAFF are not clustered on the same chromosome. APRIL is located on chromosome 17 (J. L. B., unpublished data) whereas BAFF maps to the distal arm of human chromosome 13 (13q34). Abnormalities in this locus were characterized in Burkitt lymphomas as the second most frequent defect (24) besides the translocation involving the myc gene into the Ig locus (25). Considering the high expression levels of BAFF-R on all Burkitt lymphoma cell lines analyzed (see Table 1), this raises the intriguing possibility that some Burkitt lymphomas may have deregulated BAFF expression, thus stimulating growth in an autocrine manner.

The role of antigen-specific B lymphocytes during the different stages of the immune response is highly dependent on signals and contacts from helper T cells and antigen-presenting cells such as dendritic cells (20). B lymphocytes first receive these signals early on during the immune response when they interact with T cells at the edge of the B cell follicles in lymphoid tissues, leading to their proliferation and differentiation into low affinity antibody forming cells (18). At the same time some antigen-specific B cells also migrate to the B cell follicle and contribute to the formation of germinal centers, another site of B cell proliferation but also affinity maturation and generation of memory B cells and high affinity plasma cells (19).

Signals triggered by another member of the TNF super family CD40L have been shown to be critical for the function of B lymphocytes at multiple steps of the T cell-dependent immune response. However, several studies clearly showed that CD40L/CD40 interaction does not account for all contact-dependent T-cell help for B cells. Indeed, CD40L-deficient T cells isolated from either knockout mice or patients with X-linked hyper IgM syndrome have been shown to sucessfully induce proliferation of B cells and their differentiation into plasma cells. Studies using blocking antibodies against CD40L showed that a subset of surface IgD positive B cells isolated from human tonsils proliferate and differentiate in response to activated T cells in a CD40-independent manner. Other members of the TNF family such as membrane-bound TNF and CD30L have also been shown to be involved in a CD40- and surface Ig-independent stimulation of B cells. Similar to our results with BAFF, it has been shown that CD40-deficient B cells can be stimulated to proliferate and differentiate into plasma cells by helper T cells as long as the surface Ig receptors are triggered at the same time. BAFF as well as CD30L and CD40L is expressed by T cells but its originality resides in its expression by dendritic cells as well as the highly specific location of its receptor on B cells which is in contrast to CD40, CD30 and the TNF receptor which expression has been descrided on many different cell. This observation suggests independent and specific BAFF-induced functions on B cells.

In support of a role for BAFF in T cell- and dendritic cell-induced B cell growth and potential maturation, we found that BAFF costimulates proliferation of blood-derived B cells concomitantly with cross-linking of the B cell receptors, and, thus, independently of CD40 signalling. Moreover, using CD19 positive B cells differentiated in vitro into a pre-plasma cell/GC-like B cell (14), we observed a costimulatory effect of BAFF on Ig secretion by these B cells in the presence of supernatant from activated T cells or a blend of IL-2, IL-4 and IL-10. Interestingly, the costimulatory effect was stronger in presence of the activated T cell supernatant when compared to the cytokine blend, suggesting additional soluble factors secreted by activated T cells involved in antibody production which can synergize with BAFF or additional BAFF itself. It is, therefore, possible that BAFF actively contributes to the differentiation of these GC-like B cells into plasma.

It is clear that BAFF can signal in both naive B cells as well as GC-commited B cells in vitro. Whether this observation will translate or not during a normal immune response will have to be addressed by proper in vivo experiments.

The biological responses induced in B cells by BAFF are distinct from that of CD40L, since proliferation triggered by CD40L was less dependent on an anti-$\mu$ costimulus (17) (and FIG. 5D). Morever, CD40L can counteract apoptotic signals in B cells following engagement of the B cell receptor (29), whereas BAFF was not able to rescue the B cell line Ramos from anti-$\mu$-mediated apoptosis, despite the fact that Ramos cells do express BAFF-R (Table 1; F. M. and J. L. B., unpublished observations). It is therefore likely that CD40L and BAFF fulfill distinct functions. In this respect, it is noteworthy that BAFF did not interact with any of 16 recombinant receptors of the TNF family tested, including CD40 (P.S and J.T, unpublished observations).

B cell growth was efficiently costimulated with recombinant soluble BAFF lacking the transmembrane domain. This activity is in contrast to several TNF family members which are active only as membrane-bound ligand such as TRAIL, FasL and CD40L. Soluble forms of these ligands have poor biological activity which can be enhanced by their cross-linking, thereby mimicking the membrane-bound ligand (15). In contrast, cross-linking Flag-tagged sBAFF with anti-FLAG antibodies or the use of membrane-bound BAFF expressed on the surface of epithelial cells did not further enhance the mitogenic activity of BAFF, suggesting that it can act systemically as a secreted cytokine, like TNF does. This is in agreement with the observation that a polybasic sequence present in the stalk of BAFF acted as a substrate for a protease. Similar polybasic sequences are also present at corresponding locations in both APRIL and TWEAK and for both of them there is evidence of proteolytic processing (30) (N.H. and J.T, unpublished observation). Although the protease responsible for the cleavage remains to be determined, it is unlikely to be the metalloproteinase responsible for the release of membrane-bound TNF as their sequence preferences differ completely (21). The multibasic motifs in BAFF (R-N-K-R) (SEQ ID NO:23), APRIL (R-K-R-R) (SEQ ID NO:24) and Tweak (R-P-R-R) (SEQ ID NO:25) are reminiscent of the minimal cleavage signal for furin (R-X-K/R-R) (SEQ ID NO:26), the prototype of a proprotein convertase family (31).

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual,* 2nd edition. (Sambrook, Fritsch and Maniatis, eds.), Cold Spring Harbor Laboratory Press, 1989; *DNA Cloning,* Volumes I and II (D. N. Glover, ed), 1985; *Oligonucleotide Synthesis,* (M. J. Gait, ed.), 1984; U.S. Pat. No. 4,683,195 (Mullis et al.,); *Nucleic Acid Hybridization* (B. D. Hames and S. J. Higgins, eds.), 1984; *Transcription and Translation* (B. D. Hames and S. J. Higgins, eds.), 1984; *Culture of Animal Cells* (R. I. Freshney, ed). Alan R. Liss, Inc., 1987; *Immobilized Cells and Enzymes,* IRL Press, 1986; *A Practical Guide to Molecular Cloning* (B. Perbal), 1984; *Methods in Enzymology,* Volumes 154 and 155 (Wu et al., eds), Academic Press, New York; *Gene Transfer Vectors for Mammalian Cells* (J. H. Miller and M. P. Calos, eds.), 1987, Cold Spring Harbor Laboratory; *Immunochemical Methods in Cell and Molecular Biology* (Mayer and Walker, eds.), Academic Press, London, 1987; *Handbook of Experiment Immunology,* Volumes I–IV (D. M. Weir and C. C. Blackwell, eds.), 1986; *Manipulating the Mouse Embryo,* Cold Spring Harbor Laboratory Press, 1986.

The following Examples are provided to illustrate the present invention, and should not be construed as limiting thereof.

EXAMPLES

The following experimental procedures were utilized in Examples 1–6.

DNA Construct for the Generation of Murine BAFF Tg Mice

Both human and murine cDNA sequences have been described previously (Schneider et al., 1999). A PCR fragment encoding full-length murine BAFF was generated by RT-PCR. First strand cDNA was synthesized from mouse lung polyA+ (Clontech, Palo Alto, Calif.) using oligo dT according to the manufacturer's protocol (GibcoBRL, Grand Island, N.Y.). The PCR reaction contained 1× Pfu buffer (Stratagene, La Jola, Calif.), 0.2 mM dNTPs, 10% DMSO, 12.5 pM primers, 5 units Pfu enzyme (Stratagene) and the following primers with Not1 restriction sites 5'-TAAGAATGCGGCCGCGGAATGGATGAGTCTGC AAA-3' [SEQ. ID. NO.: 19] and 5'-TAAGAATGCGGC CGCGGGATCACGCACTCCAGCAA-3' [SEQ. ID. NO.: 20]. The template was amplified for 30 cycles at 94° C. for 1 min, 54° C. for 2 min and 72° C. for 3 min followed by a 10 min extension at 72° C. This sequence corresponds to nucleotides 214 to 1171 of the GenBank file AF119383. The PCR fragment was digested with Not1 and then cloned into a modified pCEP4 vector (Invitrogen, Carlsbad, Calif.). The fragment containing murine BAFF was removed with Xba1 in order to include the SV40 polyA addition site sequence. This fragment was cloned into a pUC based vector where the promoter sequence was added. The promoter, a 1 Kb blunt Bg12-Not1 fragment containing the human ApoE enhancer and AAT (alpha anti-trypsin) promoter was purified from the plasmid clone 540B (a kind gift from Dr. Katherine Parker Ponder, Washington University, St. Louis, Mo.). An EcoRV/Bg12 fragment was purified from the final vector and used for the generation of transgenic mice. The injected offspring of C57BL/6J female×DBA/2J male F1 (BDF1) mice were backcrossed onto C57BL/6 mice. Techniques of microinjection and generation of transgenic mice have been previously described (Mcknights et al., 1983).

Analytical Methods:

Serum samples were subject to reduced SDS-PAGE analysis using a linear 12.5% gel. Total RNA from mouse liver was prepared and processed for Northern Blot analysis using an isolation kit from Promega (Madison, Wis.) according to the manufacturer's guidelines. BAFF transgene-specific mRNA was detected using a probe spanning the SV40 poly A tail of the transgene construct and obtained by digestion of the modified pCEP4 vector with Xba1 and BamH1. The probe recognizes a 1.8–2 Kd band corresponding to mRNA from the BAFF transgene. PCR analysis of tail DNA from BAFF Tg mice was carried using 12.5 pM of the following primers 5'-GCAGTTTCACAGCGATGTCCT-3' [SEQ. ID. NO.: 21] and 5'-GTCTCCGTTGCG TGAAATCTG-3' [SEQ. ID. NO.: 22] in a reaction containing 1× Taq polymerase buffer (Stratagene), 0.2 nM dNTPs, 10% DMSO and 5 units of Taq polymerase (Stratagene). A 719 bp of the transgene was amplified for 35 cycles at 94° C. for 30 sec., 54° C. for 1 min. and 72° C. for 1.5 min. followed by a 10 min. extension at 72° C.

The presence of proteins in mouse urine was measured using Multistix 10 SG reagent strips for urinalysis (Bayer Corporation, Diagnostics Division, Elkhart, Ind.).

Cell-dyn and Cytofluorimetric Analysis (FACS).

Differential WBC counts of fresh EDTA anticoagulated whole blood were performed with an Abbott Cell Dyne 3500 apparatus (Chicago, Ill.). For FACS analysis, Fluorescein (FITC)-, Cy-chrome- and Phycoerythrin-(PE)-labeled rat anti-mouse antibodies: anti-B220, anti-CD4, anti-CD8, anti-CD43, anti-IgM, anti-CD5, anti-CD25, anti-CD24, anti-CD38, anti-CD21, anti-CD44, anti-L-selectin and hamster anti-Bcl-2/control hamster Ig kit were purchased from Pharmingen (San Diego, Calif.). Production of recombinant E. coli as well as mammalian cell-derived human and mouse Flag-tagged BAFF were previously described (Schneider et al., 1999). All antibodies were used according to the manufacturer's specifications. PBL were purified from mouse blood as follows: mouse blood was collected in microtubes containing EDTA and was diluted ½ with PBS. Five hundred µl of diluted blood was applied on top of 1 ml of ficoll (Celardane, Hornby, Ontario, Canada) in a 4 ml glass tube, the gradient was performed at 2000 rpm for 30 min at room temperature and the interface containing the lymphocytes was collected and washed twice in PBS prior to FACS staining. Spleen, bone marrow and mesenteric lymph nodes were ground into a single cell suspension in RPMI medium (Life Technologies, Inc., Grand Island, N.Y.) and washed in FACS buffer (PBS supplemented with 2% fetal calf serum (JRH Biosciences, Lenexa, Kans.). Cells were first suspended in FACS buffer supplemented with the following blocking reagents: 10 µg/ml human Ig (Sandoz, Basel, Switzerland) and 10 µg/ml anti-mouse Fc blocking antibody (Pharmingen) and incubated 30 min on ice prior to staining with fluorochrome-labeled antibodies. All antibodies were diluted in FACS buffer with the blocking reagent mentioned above. Samples were analyzed using a FACScan cytofluorometer (Becton Dickinson).

Detection of Total Mouse Ig and Rheumatoid Factors in Mouse Sera by ELISA Assays.

ELISA plates (Corning glass works, Corning, N.Y.) were coated overnight at 4° C. with a solution of 10 µg/ml of goat anti-total mouse Ig (Southern Biotechnology Associates, Inc. Birmingham, Ala.) in 50 mM sodium bicarbonate buffer pH 9.6. Plates were washed 3 times with PBS/0.1% Tween and blocked overnight with 1% gelatin in PBS. One hundred µl/well of serum serial dilutions or standard dilutions was added to the plates for 30 min at 37° C. Mouse Ig were detected using 100 µl/well of a 1 µg/ml solution of an Alkaline Phosphatase (AP)-labeled goat anti-total mouse Ig (Southern Biotechnology Associates) for 30 min at 37° C. After a last wash, 3 times with PBS/0.1% Tween, the enzymatic reaction was developed using a solution of 10 µg/ml of p-nitrophenyl phosphate (Boehringer Mannheim, Indianapolis, Ind.) in 10% diethanolamine. The reaction was stopped by adding 100 µl of 3N NaOH/well. The optical density (O.D.) was measured at 405 nm using a spectrophotometer from Molecular Devices (Sunnyvale, Calif.). Standard curves were obtained using purified mouse Ig purchased from Southern Biotechnology Associates. In the case of detection of rheumatoid factors (RF), the plates were coated with normal goat Ig (Jackson ImmunoResearch laboratories, Inc., West Grove, Pa.) instead of goat anti-mouse Ig and detection of mouse Ig was performed as described above. Detection of mouse isotypes in the RF assay was done using AP-labeled goat anti-mouse IgA, IgM, IgG2a, IgG2b and IgG3, as well as purified mouse IgA, IgM, IgG2a, IgG2b and IgG3 for standard curves (Southern Biotechnology Associates Inc.). All statistical comparisons were performed by analysis of variance.

Detection of Circulating Immune Complexes (CIC) and Precipitation of Cryoglobulins in Mouse Sera.

The assay was performed as previously described (June et al., 1979; Singh and Tingle, 1982) with the following modifications: ELISA plates (Corning glass works) were coated overnight at 4° C. with 5 µg/ml of human C1q (Quidel, San Diego, Calif.) in 50 mM sodium bicarbonate buffer pH 9.6. The plates were washed 3 times with PBS/0.1% Tween. Fifty µl/well of 0.3 M EDTA was added to the plates plus 50 µl/well of serum serial dilutions or solutions of known concentrations of a standard immune complex (peroxidase-mouse anti-peroxidase (PAP) from DAKO (Carpinteria, Calif.). The plates were incubated 30 min at 37° C. The plates were washed 3 times with PBS/0.1% Tween. Mouse Ig in the immune complexes were detected using 100 µl/well of a 1 µg/ml solution of an AP-labeled goat anti-mouse Ig (Southern Biotechnology Associates, Inc.) as described above for the ELISA assays. Cryoglobulins were detected by incubating overnight at 4° C. mouse serum diluted ⅟15 in water and precipitates were scored visually.

Anti-Double Stranded (ds) and Single Stranded (ss) DNA Assays.

Anti-ssDNA were performed using NUNC-immuno Plate MaxiSorp plates (NUNC A/S, Denmark). Plates were coated overnight at 4° C. first with 100 μg/ml methylated BSA (Calbochem Corp., La Jolla, Calif.), then with 50 μg/ml grade I calf thymus DNA (Sigma, St. Louis, Mo.). The calf thymus DNA was sheared by sonication and then digested with S1 nuclease before use. For the anti-ssDNA assay, the DNA was boiled for 10 min and chilled on ice before use. After blocking, serial dilutions of the serum samples were added and incubated at room temperature for 2 h. Autoantibodies were detected with goat anti-mouse IgG-AP (Sigma) and develop as described above for the ELISA assays. Standard curves were obtained using known quantities of anti-DNA mAb 205, which is specific for both ss- and dsDNA (Datta et al., 1987).

Immunohistochemistry

Spleen and lymph nodes were frozen in O.C.T. embedding medium (Miles, Elkhart, Ind.) and mounted for cryostat sectioning. Sections 7–10 μm thick were dried and fixed in acetone. All Ab incubations (10 μg/ml) were done for 1 hr at room temperature in a humidified box after dilution in Tris-buffered saline A (TBS-A, 0.05M Tris, 0.15M NaCl, 0.05% Tween-20 (v/v), 0.25% BSA), rinsed in TBS-B (0.05M Tris, 0.15M NaCl, 0.05% Tween-20) and fixed 1 min in methanol before initiating the enzymatic reaction. Horseradish peroxidase (HRP) and alkaline phosphatase (AP) activities were developed using the diaminobenzidine (DAB) tablet substrate kit (Sigma) and the 5-bromo-4-chloro-3-indolyl phosphate/nitro blue tetrazolium (BCIP/NBT, Pierce, Rockford, Ill.), respectively. Stained tissue sections were finally fixed 5 min in methanol and counter stained with Giemsa (Fluka, Buchs, Switzerland). Biotin-labeled antibodies rat anti-B220, anti-CD11c, anti-syndecan-1 as well as unlabeled rat anti-CD4, anti-CD8α and anti-CD8β were purchased from Pharmingen. Biotin-labeled peanut agglutinin (PNA) was obtained from Vector laboratories (Burlingame, Calif.). (HRP)-labeled mouse anti-rat Ig and (HRP)-streptavidin were purchased from Jackson ImmunoResearch laboratories, Inc. and AP-labeled streptavidin from Southern Biotechnology Associates, Inc. In the case of immunohistochemistry on kidney tissue to detect Ig deposition, paraffin section were used, dewaxed and blocked using diluted horse serum from Vector (Burlingame, Calif.), followed by staining with HRP-goat anti-mouse Ig from Jackson Immunoresearch. Detection was performed as described above.

Example 1

BAFF Transgenic (BAFF Tg) Founder Mice have an Abnormal Phenotype.

Full length murine BAFF was expressed in transgenic mice using the liver specific alpha-1 antitrypsin promoter with the APO E enhancer. The full length version was chosen with the expectation that BAFF would be either cleaved and act systemically or if retained in a membrane bound form that local liver specific abnormalities would be observed possibly providing functional clues. We obtained 13 founder mice positive for the BAFF transgene (Table 2). Four of these mice died at a young age. Routine pathology was carried out on mice 811 and 816 (Table 2). There was no obvious infection in these mice; however, cardiovascular and renal abnormalities were apparent and similar to those described for severe hypertension (Fu, 1995) (Table 2). Hematoxylin and eosin (H&E)-stained kidney tissue sections of founder 816 showed that the morphology of glomeruli in that mouse was abnormal, whereas the rest of the kidney tissue seemed normal (data not shown). Many BAFF transgenic founder mice had proteinuria (Table 2). Immunohistochemistry on spleen frozen tissue sections from mouse 816, revealed an abnormal and extensive B cell staining and reduced staining for T cells and this observation was confirmed in the progeny (see below, FIG. 12).

Using two color FACS analysis, the ratio of % B220 positive B cells over % CD4 positive T cells was calculated. This ratio was two to seven times higher in BAFF Tg founder mice when compared to control negative BDF1 mice (Table 2), suggesting an increase of the B cell population in BAFF Tg mice. We selected nine of these founder mice to generate our different lines of transgenic mice as underlined in Table 2. None of the remaining BAFF Tg founder mice or the derived progeny showed any signs of ill health months after the early death of founders 696, 700, 811 and 816, suggesting that these 4 mice might have expressed higher levels of BAFF which caused their death. BAFF overexpression in the liver of transgenic mice was confirmed by Northern blot analysis (data not shown). In all BAFF-Tg mice examined histologically, the livers showed no abnormalities indicating that local overexpression of BAFF did not induce any immunological or pathological events. An ELISA assay for murine BAFF is not available; however, we showed that 2% serum from BAFF Tg mice, but not from control mice, blocked the binding of mammalian cell-derived mouse soluble Flag-tagged BAFF to BJAB cells. Moreover, 5% serum from BAFF Tg mice but not from control mice increased the proliferation of human B cells from PBL in the presence of anti-μ (data not shown). These data suggest that substantial amounts of soluble BAFF are present in the blood of BAFF Tg.

Example 2

Peripheral Lymphocytosis in BAFF Tg Mice is Due to Elevated B Cell Numbers

Figure 7C:
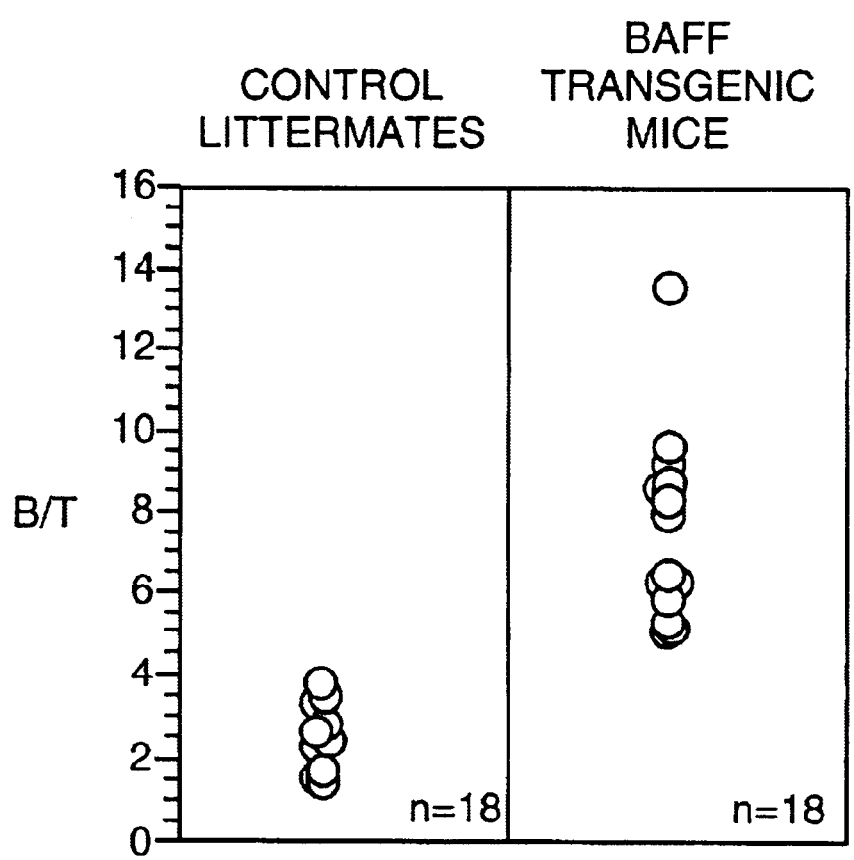
Figure 7E:
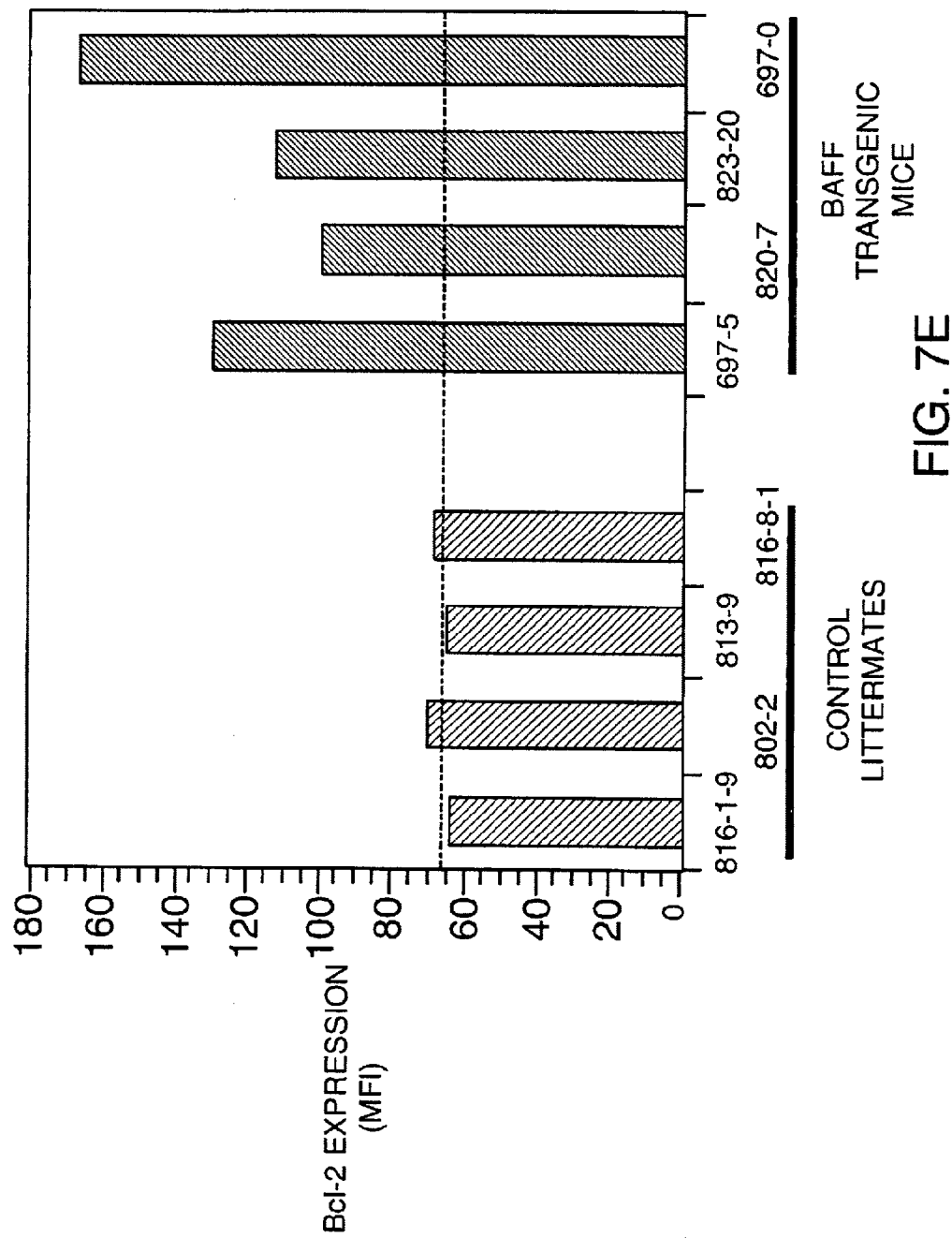
Figure 7F:
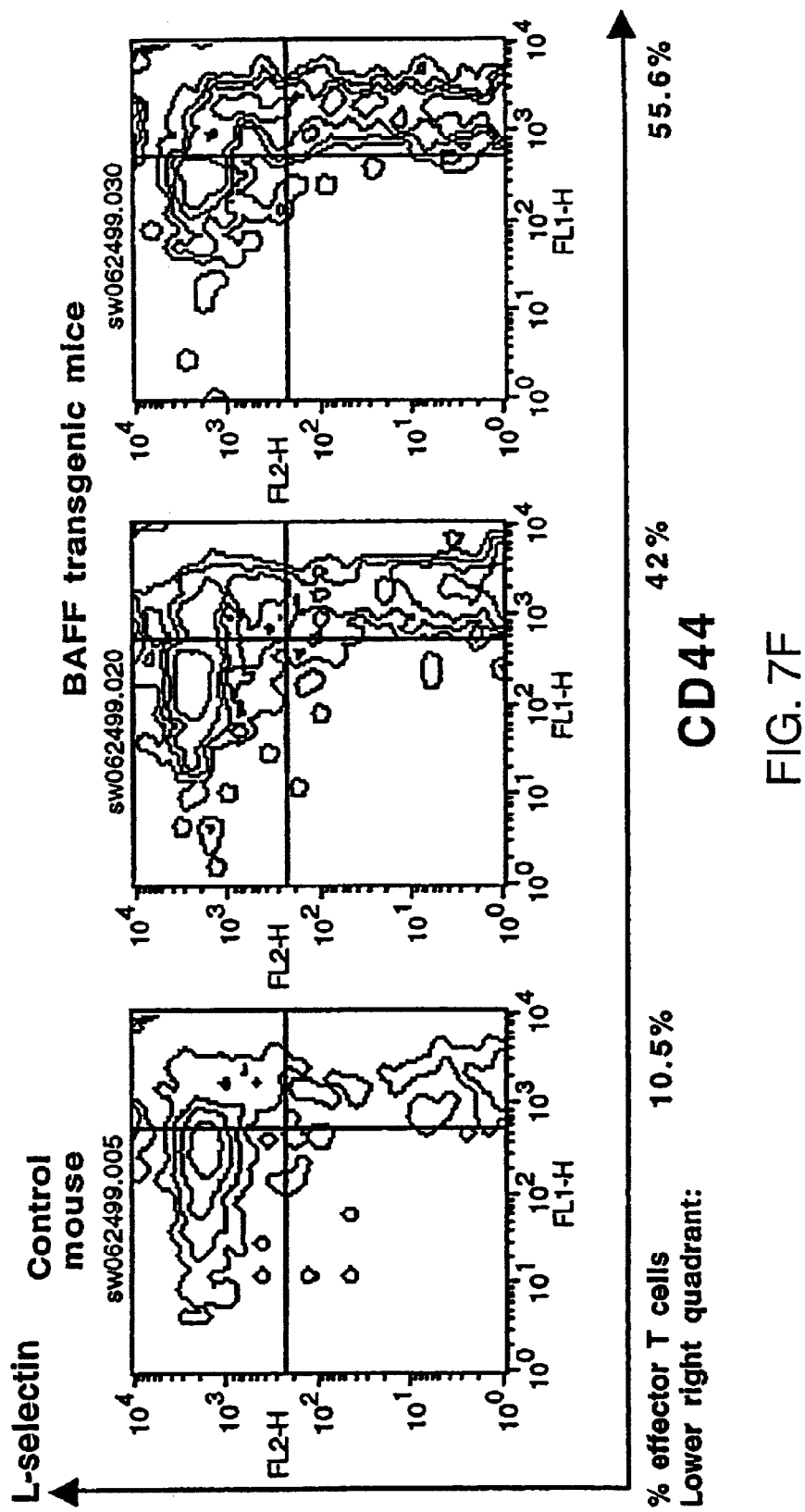

The transgenic mice population was found to have more lymphocytes in the blood when compared to control negative littermates, reaching values as high as 13000 lymphocytes/μl of blood (FIG. 7A). In contrast, the number of granulocytes per μl of blood in both BAFF Tg mice and control mice remained within normal limits (FIG. 7A). Since FACS analysis, using anti-CD4 and anti-B220 antibodies, of peripheral blood cells (PBL) from 18 BAFF Tg mice issued from six different founder mice showed increased B/T ratios (FIGS. 7B and 7C), the elevated lymphocyte levels resulted from an expanded B cell subset. Likewise, using this method, calculation of absolute numbers of CD4 circulating T cells revealed a 50% reduction of this T cell subset in BAFF Tg mice when compared to control mice, and the same observation was made for the CD8 T cell subset (data not shown). All B cells from the PBL of BAFF Tg mice have increased MHC class II and Bcl-2 expression when compared to B cells from control mice (FIGS. 7D and 7E, respectively), indicating some level of B cell activation in PBL of BAFF Tg mice. T cells in the blood of BAFF Tg mice did not express the early activation markers CD69 or CD25; however, 40 to 56% of CD4 or CD8 T cells were activated effector T cells with a $CD44^{hi}$, L-selectin$^{lo}$ phenotype versus only 8% to 12% in control littermates (FIG. 7F). Thus BAFF Tg mice clearly show signs of B cell lymphocytosis and global B cell activation along with T cell alterations.

Example 3

Expanded B Cell Compartments are Composed of Mature Cells.

Figures 3, 8A:
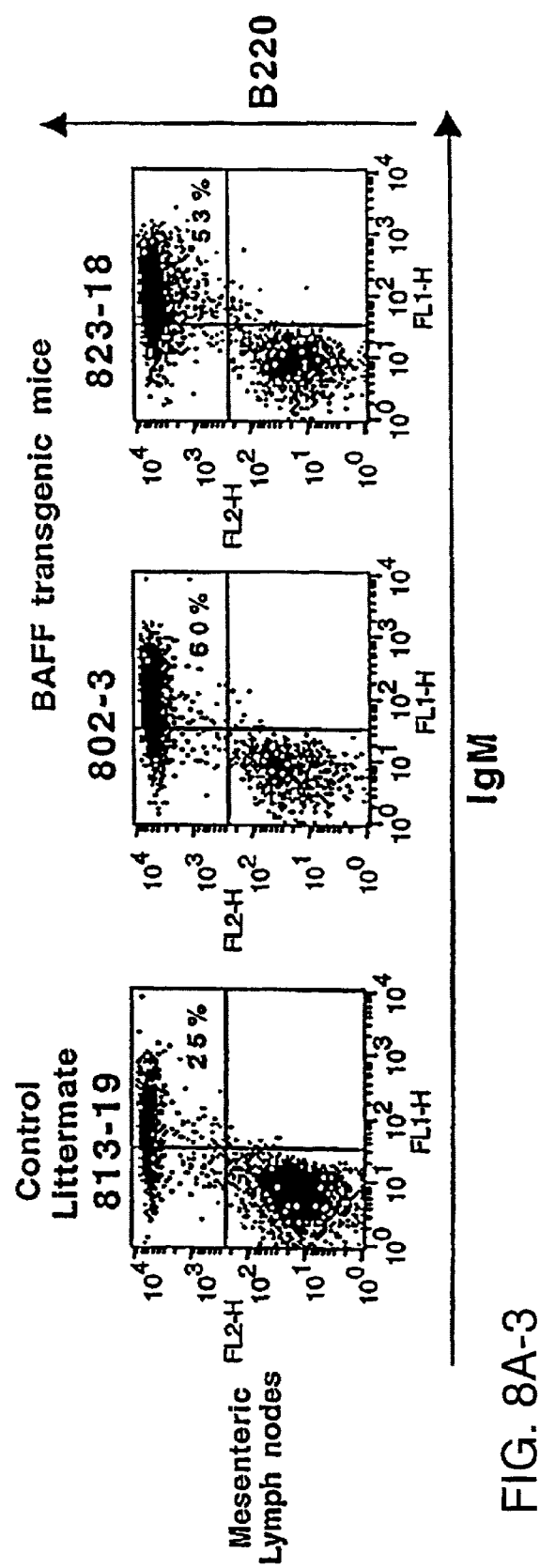
Figure 8B:
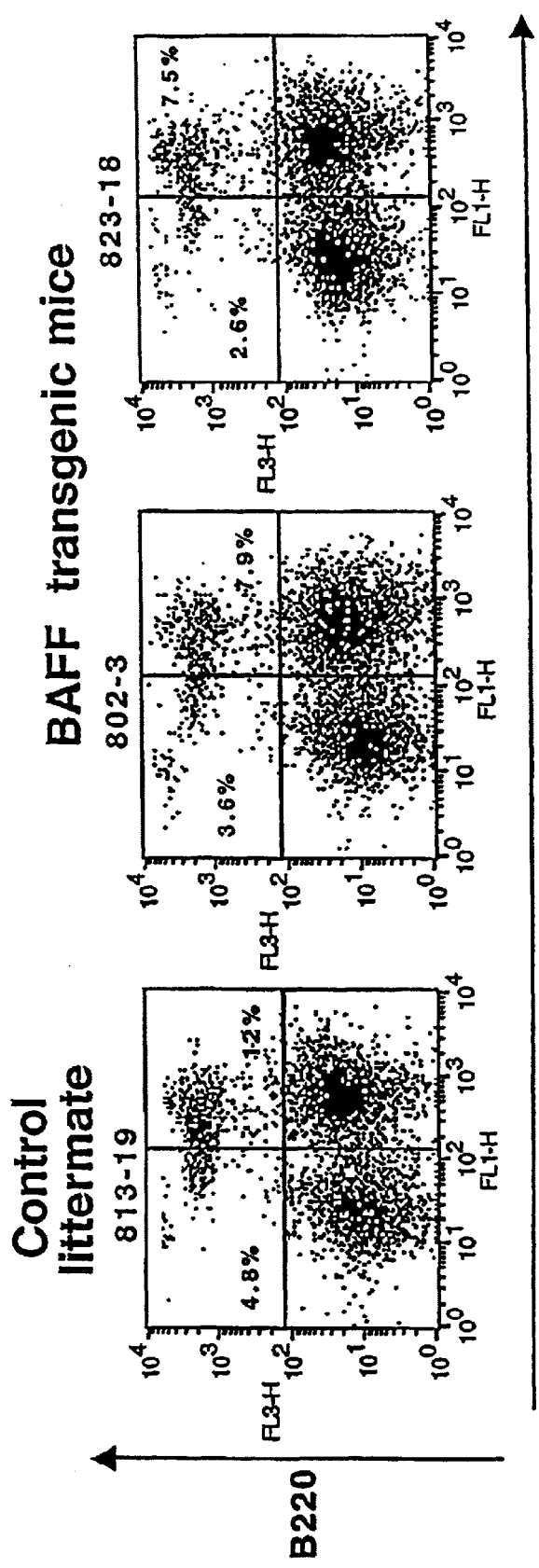

To see whether overexpression of BAFF in the transgenic mice was affecting the B cell compartment centrally in the bone marrow and peripherally in secondary lymphoid organs, we examined by FACS the spleen, bone marrow and mesenteric lymph nodes from a total of seven BAFF Tg mice and seven control littermates derived from four different founder mice. The mature B cell compartment was analyzed by staining with both anti-B220 and anti-IgM antibodies. Two representative BAFF Tg mice and one representative control littermate are shown in FIG. 8. The mature B cell compartment (IgM+. B220+) was increased in both the spleen and the mesenteric lymph nodes (FIG. 8A, top and bottom panels, respectively). Analysis of B220+/IgM+ B cells (FIG. 7A, middle panel) or the proB cell (CD43+/B220+) and the preB cell (CD43−/B220+) compartments in the bone marrow (FIG. 8B) showed that BAFF Tg mice and control littermates were similar. These data indicate that overexpression of BAFF is affecting the proliferation of mature B cells in the periphery but not progenitor B cells in the bone marrow. Analysis by FACS of the B cell subpopulations in the spleen, revealed an increased proportion of marginal zone (MZ) B cells in BAFF Tg mice when compared to control mice (Table 3). The population of follicular B cells remained proportional in both BAFF Tg and control mice whereas the fraction of newly formed B cells is slightly decreased in BAFF Tg mice (Table 3). This result was also confirmed on B220+ splenic B cells using anti-CD38 versus anti-CD24 antibodies and anti-IgM versus anti-IgD antibodies and analyzing for at the $CD38^{hi}/CD24^+$ and $IgM^{hi}/IgD^{lo}$ for the MZ B cell population, respectively, as previously described (Oliver et al., 1997)(data not shown). Immunohistochemical analysis using an anti-mouse IgM antibody revealed the expansion of the IgM-bright MZ B cell area in the spleen of BAFF Tg mice when compared to control mice (data not shown). All BAFF Tg $B220^+0$ splenic B cells also express higher levels of MHC class II (Table 3) and Bcl-2 (data not shown) compared to splenic B cells from control mice, indicating that splenic B cells as well as B cells from PBL are in an activated state.

Example 4
BAFF Tg Mice have High Levels of Total Immunoglobulins, Rheumatoid Factors and Circulating Immune Complexes in their Serum.

Figure 9A:
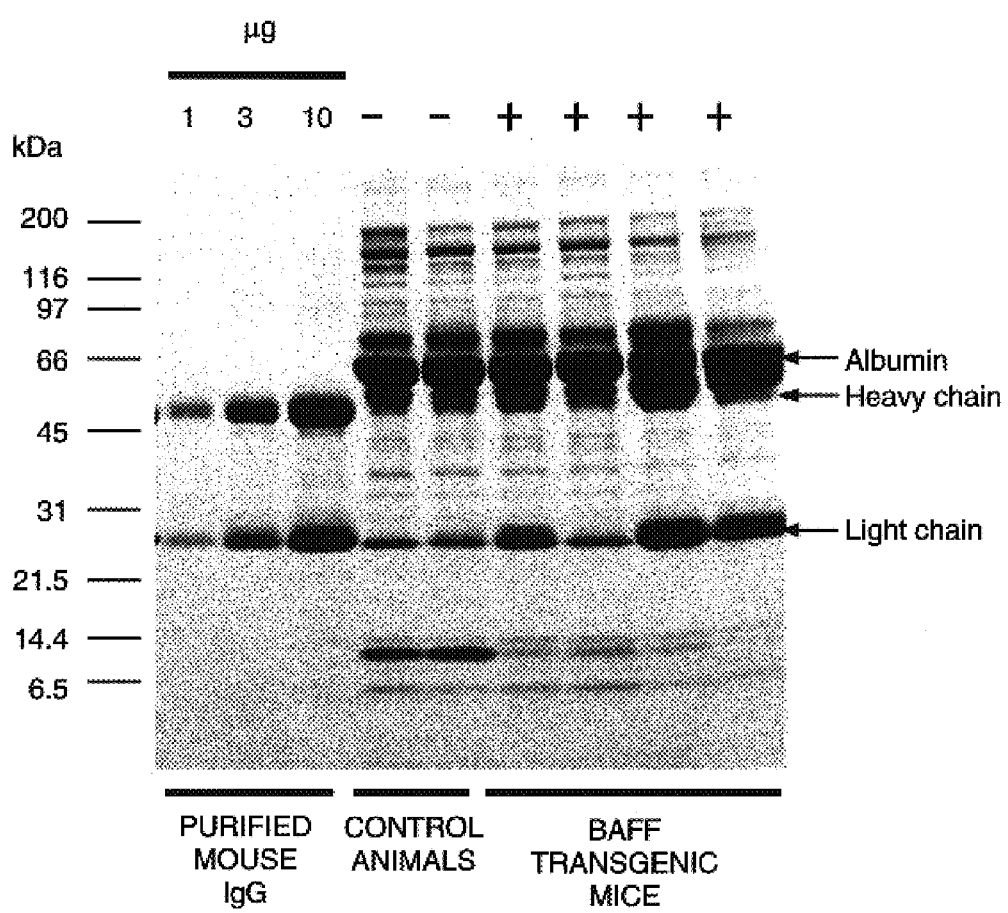
Figure 9B:
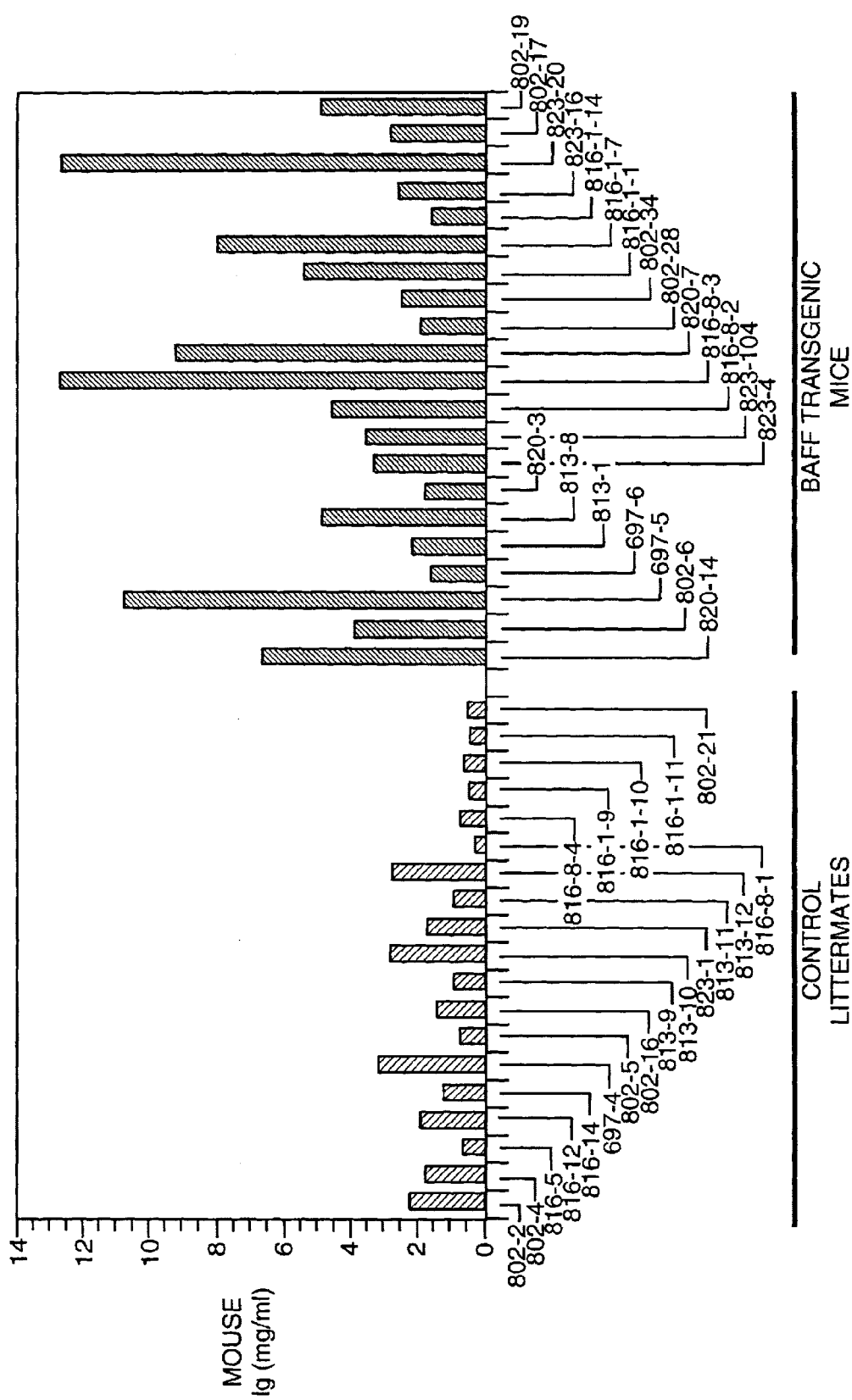

The increased B cell compartment in BAFF Tg mice suggested that the level of total Ig in the blood of these animals might also be increased. SDS-PAGE, analysis of serum from BAFF Tg mice and control littermates showed that the heavy and light chains IgG bands were at least fold more intense in 3 out of 4 BAFF Tg mice compared to the control sera (FIG. 9A). Likewise, an ELISA determination on the sera from BAFF Tg mice show significantly higher total Ig levels when compared to that of the control mice (FIG. 9B).

Figure 9C:
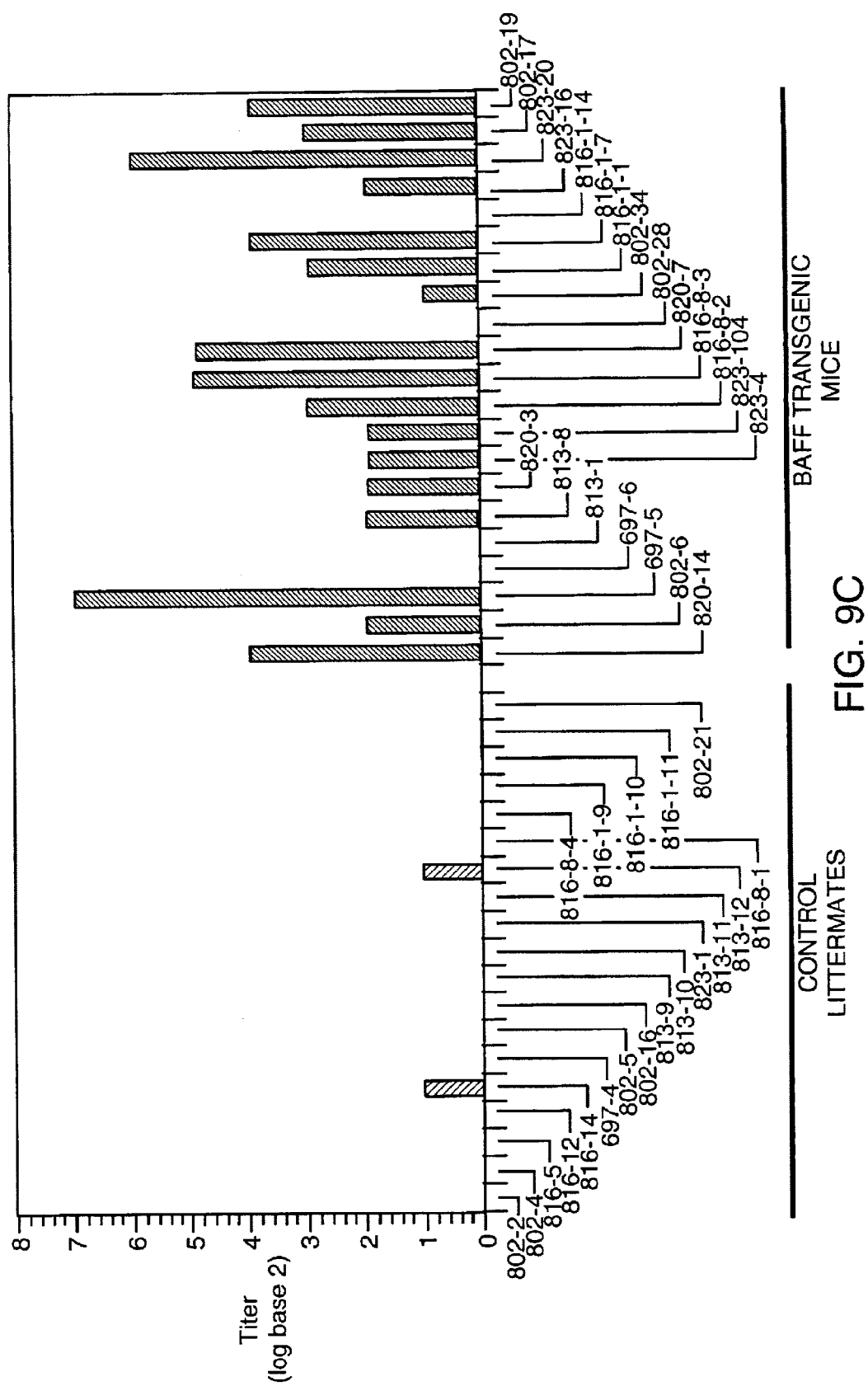

Despite the high levels seen by SDS-PAGE, the excessively high levels of Ig seen by ELISA determination in some mice, e.g., 697-5, 816-8-3 and 823-20, led us to suspect the presence of rheumatoid factors (RF) in the sera, or autoantibodies directed against antigenic determinants on the Fc fragment of IgG (Jefferis, 1995). These antibodies could bind to the goat anti-mouse Ig used to coat the ELISA plates and give erroneously high values. ELISA plates were coated with normal irrelevant goat Ig and the binding of BAFF Tg Ig to normal goat Ig was measured. FIG. 9C shows that sera from most BAFF Tg mice contained Ig reacting with normal goat Ig, whereas only two out of 19 control mice exhibited reactivity in the same assay. These RF were mainly of the IgM, IgA and IgG2a isotypes (data not shown).

Figure 9D:
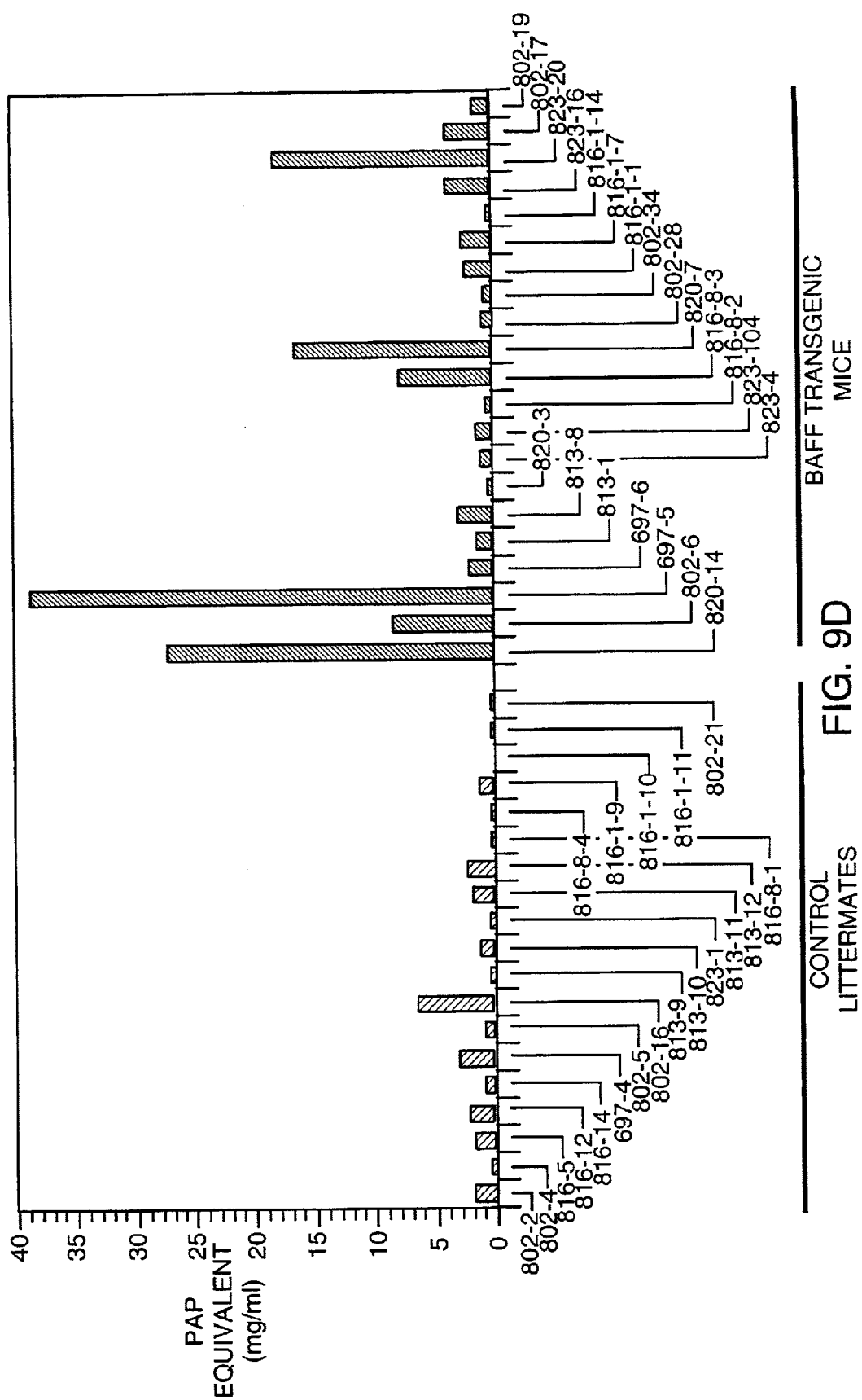

Presence of RF can be associated with the presence of high levels of circulating immune complexes (CIC) and cryoglobulin in the blood (Jefferis, 1995). To verify whether or not BAFF Tg mice have abnormal serum levels of CIC, a C1q-based binding assay was used to detect CIC in the 21 BAFF Tg mice analyzed above. Only 5 BAFF Tg showed significantly high levels of CIC when compared to control mice, nonetheless these mice corresponded to the animals having the highest total Ig and rheumatoid factor levels (FIG. 9D). We also observed precipitate formation when BAFF Tg mice sera were diluted ¹⁄₁₅ in water but not control sera indicating the presence of cryoglobulin in these mice (data not shown). Thus, in addition to B cell hyperplasia, BAFF Tg mice display severe hyperglobulinemia associated with RF and CIC.

Example 5
Some BAFF Tg Mice have High Levels of Anti-Single Stranded (ss) and Double-Stranded (ds) DNA Autoantibodies.

Figure 10A:
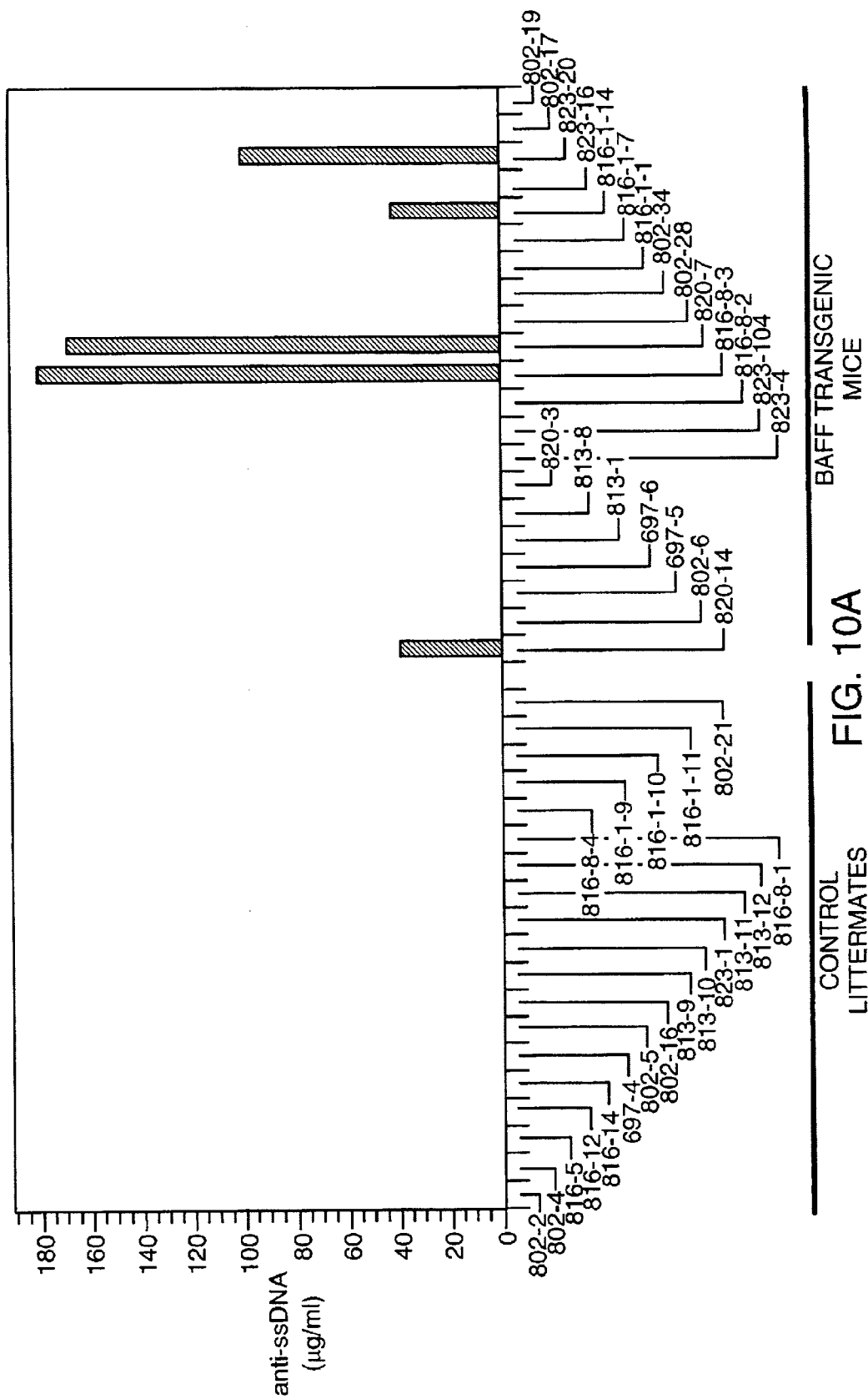
Figure 10C:
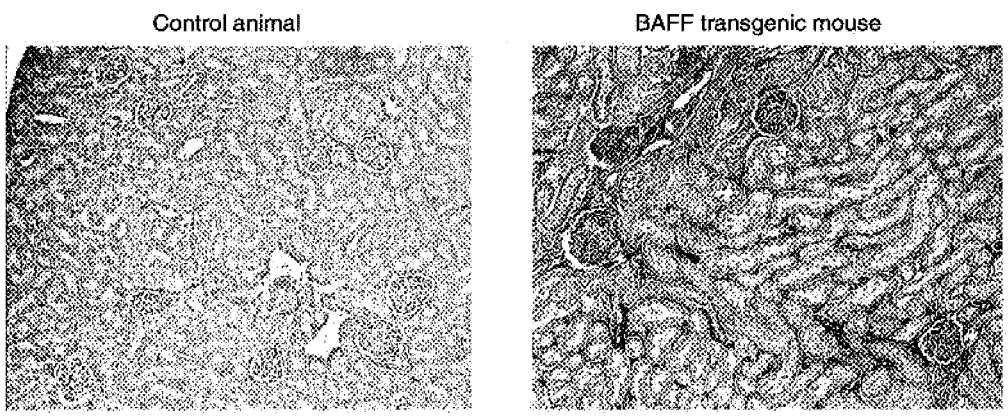

Initially, we observed kidney abnormalities reminiscent of a lupus-like disease in two of our founder mice (Table II). The presence of anti-DNA autoantibodies have also been described in SLE patients or the SLE-like (SWR×NZB)F1 (SNF1) mouse (Datta et al., 1987). Anti-ssDNA autoantibody levels were detected in BAFF Tg mice previously shown to have the highest level of total serum Ig (FIG. 10A). We analyzed the serum of two BAFF Tg mice negative for antibodies against ssDNA (697-5 and 816-1-1) and three transgenic mice secreting anti-ssDNA antibodies (820-14, 816-8-3 and 820-7) for the presence of anti-dsDNA antibodies in parallel with five control littermates. BAFF Tg mice also secreted anti-dsDNA, however, the levels of secretion did not always correlate with that of anti-ssDNA antibodies, as serum from BAFF Tg mouse 697-5 which did not contain detectable levels of anti-ssDNA antibodies, was clearly positive for the presence of anti-dsDNA (FIG. 10B). Therefore, BAFF Tg mice showing the most severe hyperglobulinemia secrete pathological levels of anti-DNA autoantibodies. Additionally, and also reminiscent of a lupus-like problem in these mice we detected immunoglobulin deposition in the kidney of six BAFF Tg mice analyzed (FIG. 10C), three of these mice did not secrete detectable levels anti-DNA antibodies (data not shown).

Example 6
BAFF Tg Mice have Enlarged B Cell Follicles, Numerous Germinal Centers, Reduced Dendritic Cell Numbers and Increased Plasma Cell Numbers in both the Spleen and Mesenteric Lymph Nodes (MLN).

BAFF Tg mice had large spleens, MLN (data not shown) and Peyer's patches (FIG. 11). Immunohistochemistry showed the presence of enlarged B cell follicles and reduced peripheral arteriolar lymphoid sheets (PALS or T cell area) in BAFF Tg mice (FIG. 12B). Interestingly, few germinal centers were observed in non-immunized control littermates (and is typical of this colony in general) and those present were small (FIG. 12C), whereas BAFF Tg mice possessed numerous germinal centers in the absence of immunization (FIG. 12D). Staining with anti-CD11c for dendritic cells in the T cell zone and the marginal zone of control mice (FIG. 12E) was considerably reduced in BAFF Tg mice (FIG. 12F). Syndecan-1-positive plasma cells were almost undetectable in the spleen from control littermates (FIG. 12G), yet the red pulp of BAFF Tg mice was strongly positive for syndecan-1 (FIG. 12H). Very similar observations were made for the MLN (FIG. 13). In the MLN of BAFF Tg mice the B cell areas were dramatically expanded (FIG. 13B) in contrast to the normal node where B cell follicles were easily recognizable at the periphery of the node under the capsule with a typical paracortical T cell zone (FIG. 13A). The medulla of MLN from BAFF Tg mice were filled with syndecan-1 positive cells which presumably are plasma cells (FIG. 13H). In conclusion, analysis of secondary lymphoid organs in BAFF Tg mice was consistent with the expanded B cell phenotype showing multiple cellular abnormalities and intense immune activity.

REFERENCES

1. Smith et al. (1994) *Cell* 76:959–962.
2. Vassalli (1992) *Annu. Rev. Immunol.* 10:411–452.
3. De Togni et al. (1994) *Science* 264:703–707.
4. Koni et al. (1997) *Immunity* 6:491–500.
5. Amakawa et al. (1996) *Cell* 84:551–562.
6. Russell et al. (1993) *Proc. Natl. Acad. Sci. USA* 90:4409–4413.
7. Zheng et al. (1995) *Nature* 377:348–351.
8. van Kooten and Banchereau (1997) *Curr. Opin. Immunol.* 9:330–337.
9. Stuber and Strober (1996). *J. Exp. Med.* 183:979–989.
10. Schneider et al. (1997) *J. Biol. Chem.* 272:18827–18833.
11. Hahne et al. (1998) *J. Exp. Med.* 188:1185–1190.
12. Hahne et al. (1996) *Science* 274:1363–1366.
13. Grimaitre et al. (1997) *Eur. J. Immunol.* 27:199–205.
14. Thome et al. (1997) *Nature* 386:517–521.
15. Schneider et al. (1998) *J. Exp. Med.* 187:1205–1213.
16. Matsudaira, P. (1987) *J. Biol. Chem.* 262:10035–10038.
17. Armitage et al. (1992) *Nature* 357:80–82.
18. Bucher et al. (1996) *Computer Chem.* 20:3–24.
19. Banner et al. (1993) *Cell* 73:431–445.
20. Nagata (1997) *Cell* 88:355–365.
21. Black et al. (1997) *Nature* 385:729–733.
22. Wong et al. (1997) *J. Biol. Chem.* 272:25190–25194.
23. Kindler and Zubler. (1997) *J Immunol.* 159:2085–2090.
24. Sonoki et al. (1995) *Leukemia* 9:2093–2099.
25. Magrath, I. (1990) *Adv Cancer Res* 55:133–270.
26. Garside et al. (1998) *Science* 281:96–99.
27. MacLennan et al. (1997) *Immunol. Rev.* 156:53–66.
28. Dubois et al. (1997). *J. Exp. Med.* 185:941–951.
29. Tsubata et al. (1993) *Nature* 364:645–648.
30. Chicheportiche et al. (1997) *J. Biol. Chem.* 272:32401–32410.
31. Nakayama (1997) *Biochem. J.* 327:625–635.
32. Jefferis, R. (1995). Rheumatoid factors, B cells and immunoglobulin genes. Br. Med. Bull. 51, 312–331.
33. Schneider et al. (1999) *J. Exp. Med.* 189, 1747–1756.
34. Mcknights et al. (1983) Cell 34, 335–341.
35. Datta et al. (1987) J. Exp. Med. 165, 1252–1261.

What is claimed is:

1. A method of inhibiting B-cell growth in an animal comprising the step of administering a therapeutically effective amount of an anti-BAFF antibody that binds human BAFF (SEQ ID NO:1), wherein B-cell growth in the animal is inhibited.

2. A method of inhibiting immunoglobulin production in an animal comprising the step of administering a therapeutically effective amount of an anti-BAFF antibody that binds human BAFF (SEQ ID NO:1), wherein immunoglobulin production in the animal is inhibited.

3. A method of co-inhibiting B-cell growth and immunoglobulin production in an animal comprising the step of administering a therapeutically effective amount of an anti-BAFF antibody that binds human BAFF (SEQ ID NO:1), wherein B-cell growth and immunoglobulin production in the animal are inhibited.

4. A method of inhibiting B-cell growth and maturation in an animal comprising the step of administering a therapeutically effective amount of an anti-BAFF antibody that binds human BAFF (SEQ ID NO:1), wherein B-cell growth and maturation in the animal are inhibited.

5. A method of inhibiting B-cell growth in an animal comprising the step of administering a therapeutically effective amount of an anti-BAFF antibody that binds murine BAFF (SEQ ID NO:2), wherein B-cell growth in the animal is inhibited.

6. A method of inhibiting immunoglobulin production in an animal comprising the step of administering a therapeutically effective amount of an anti-BAFF antibody that binds murine BAFF (SEQ ID NO:2), wherein immunoglobulin production in the animal is inhibited.

7. A method of co-inhibiting B-cell growth and immunoglobulin production in an animal comprising the step of administering a therapeutically effective amount of an anti-BAFF antibody that binds murine BAFF (SEQ ID NO:2), wherein B-cell growth and immunoglobulin production in the animal are inhibited.

8. A method of inhibiting B-cell growth and maturation in an animal comprising the step of administering a therapeutically effective amount of an anti-BAFF antibody that binds murine BAFF (SEQ ID NO:2); wherein B-cell growth and maturation in the animal are inhibited.

9. The method according to any one of claims 1–8, wherein the anti-BAFF antibody is a monoclonal antibody.

10. The methods of claim 9, wherein the antibody is recombinantly produced.

11. The method as in claim 9, wherein the antibody is a chimeric antibody.

12. The method as in claim 9, wherein the antibody is a humanized antibody.

13. The method as in claim 9, wherein the antibody comprises human constant domains.

14. The method as in claim 9, wherein the antibody is a F(ab')$_2$ fragment.

* * * * *

Adverse Decision in Interference

Patent No. 6,869,605, Jeffrey Browning, Christine Ambrose, Fabienne Mackay, Jurg Tschopp, Pascal Schneider, BAFF, INHIBITORS THEREOF AND THEIR USE IN THE MODULATION OF B-CELL RESPONSE, Interference No. 105,485, final judgment adverse to the patentees rendered July 17, 2008 as to claims 1-14.

*(Official Gazette February 17, 2009)*